United States Patent
McWherter et al.

(10) Patent No.: US 10,098,843 B2
(45) Date of Patent: *Oct. 16, 2018

(54) COMPOSITIONS OF 5-ETHYL-2-{4-[4-(4-TETRAZOL-1-YL-PHENOXYMETHYL)-THIAZOL-2-YL]-PIPERIDIN-1-YL}-PYRIMIDINE

(71) Applicant: Cymabay Therapeutics, Inc., Newark, CA (US)

(72) Inventors: Charles A. McWherter, Hayward, CA (US); Robert Louis Martin, Hayward, CA (US); David B. Karpf, Monte Sereno, CA (US); Brian K. Roberts, Hayward, CA (US); Douglas Alan Lorenz, Bend, OR (US); Rodney James Ketner, Bend, OR (US)

(73) Assignee: CymaBay Therapeutics, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/002,498

(22) Filed: Jan. 21, 2016

(65) Prior Publication Data

US 2016/0213618 A1    Jul. 28, 2016

Related U.S. Application Data

(63) Continuation of application No. 13/165,651, filed on Jun. 21, 2011, now Pat. No. 9,241,924.

(Continued)

(51) Int. Cl.
*A61K 9/16* (2006.01)
*C07D 417/14* (2006.01)
(Continued)

(52) U.S. Cl.
CPC .......... *A61K 9/1652* (2013.01); *A61K 9/2054* (2013.01); *A61K 31/397* (2013.01); *A61K 31/506* (2013.01); *C07D 417/14* (2013.01); *A61K 9/1635* (2013.01); *A61K 9/1641* (2013.01); *A61K 9/2018* (2013.01)

(58) Field of Classification Search
None
See application file for complete search history.

(56) References Cited

U.S. PATENT DOCUMENTS

| 3,536,809 A | 10/1970 | Applezweig |
| 3,598,123 A | 8/1971 | Zaffaroni |
| (Continued) | | |

FOREIGN PATENT DOCUMENTS

| CL | 27752002 | 6/2001 |
| CL | 28992000 | 7/2001 |
| (Continued) | | |

OTHER PUBLICATIONS

U.S. Appl. No. 13/006,298, filed Jan. 13, 2011, Song, et al.
(Continued)

*Primary Examiner* — Bethany P Barham
*Assistant Examiner* — Dominic Lazaro
(74) *Attorney, Agent, or Firm* — Foley & Lardner LLP; Photon Rao

(57) ABSTRACT

This invention relates to the field of pharmaceutical chemistry and, more specifically, to pharmaceutical formulations as well as to intermediates used to prepare such formulations and to methods for manufacturing such formulations.

15 Claims, 11 Drawing Sheets

*In vitro* Dissolution Results for 25% Compound A:CAP SDD and Crystalline Compound A

Related U.S. Application Data

(60) Provisional application No. 61/357,981, filed on Jun. 23, 2010.

(51) Int. Cl.
*A61K 31/506* (2006.01)
*A61K 9/20* (2006.01)
*A61K 31/397* (2006.01)

(56) References Cited

U.S. PATENT DOCUMENTS

| | | | |
|---|---|---|---|
| 3,778,443 A | 12/1973 | Arya | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,673,564 A | 6/1987 | Kawata et al. | |
| 4,894,235 A | 1/1990 | Kohne et al. | |
| 5,013,556 A | 5/1991 | Woodle et al. | |
| 5,340,591 A | 8/1994 | Nakano et al. | |
| 5,420,298 A | 5/1995 | Edwards et al. | |
| 5,456,923 A | 10/1995 | Nakamichi et al. | |
| 5,707,646 A | 1/1998 | Yajima et al. | |
| 5,817,667 A | 10/1998 | Chu et al. | |
| 5,817,677 A | 10/1998 | Linz et al. | |
| 5,939,099 A | 8/1999 | Grabowski et al. | |
| 6,020,346 A | 2/2000 | Armour et al. | |
| 6,051,712 A | 4/2000 | Binggeli et al. | |
| 6,221,660 B1 | 4/2001 | Bonini et al. | |
| 6,274,735 B1 | 8/2001 | Lohri et al. | |
| 6,468,756 B1 | 10/2002 | Bonini et al. | |
| 7,108,991 B2 | 9/2006 | Chen et al. | |
| 7,638,541 B2 | 12/2009 | Chen et al. | |
| 8,183,381 B2 | 5/2012 | Ma et al. | |
| 8,277,495 B2 | 10/2012 | Demetriou et al. | |
| 2002/0009494 A1* | 1/2002 | Curatolo | A61K 9/146 424/489 |
| 2002/0099214 A1 | 7/2002 | Gibson et al. | |
| 2002/0198223 A1 | 12/2002 | Allerton et al. | |
| 2003/0064990 A1 | 4/2003 | Denton et al. | |
| 2003/0185893 A1 | 10/2003 | Beyerinck et al. | |
| 2004/0024218 A1 | 2/2004 | Barlocco et al. | |
| 2005/0165005 A1 | 7/2005 | Genevois-Borella et al. | |
| 2006/0135501 A1 | 6/2006 | Knox et al. | |
| 2006/0142262 A1 | 6/2006 | Jones et al. | |
| 2006/0155128 A1 | 7/2006 | Jones et al. | |
| 2008/0038340 A1* | 2/2008 | Kusaki | A61K 9/1623 424/464 |
| 2009/0054475 A1* | 2/2009 | Chen | C07D 401/04 514/275 |
| 2009/0137590 A1 | 5/2009 | Ma et al. | |
| 2009/0270404 A1 | 10/2009 | Wilson et al. | |
| 2010/0087465 A1 | 4/2010 | Chen et al. | |
| 2010/0130511 A1 | 5/2010 | Chen et al. | |
| 2011/0137032 A1 | 6/2011 | Endo et al. | |
| 2011/0152270 A1 | 6/2011 | Song et al. | |
| 2011/0160222 A1 | 6/2011 | Chen et al. | |
| 2011/0263617 A1 | 10/2011 | Mark et al. | |
| 2011/0294836 A1 | 12/2011 | Song et al. | |
| 2011/0313160 A1 | 12/2011 | Chen et al. | |
| 2011/0318418 A1 | 12/2011 | McWherter et al. | |
| 2012/0184572 A1 | 7/2012 | Song et al. | |

FOREIGN PATENT DOCUMENTS

| | | | |
|---|---|---|---|
| CL | 21302008 | 1/2009 | |
| CL | 21312008 | 1/2009 | |
| CL | 20932008 | 5/2009 | |
| CL | 21382008 | 10/2009 | |
| CL | 21392008 | 10/2009 | |
| DE | 27 01 705 A1 | 8/1977 | |
| EP | 0 630 887 A1 | 12/1994 | |
| EP | 0 755 923 A1 | 1/1997 | |
| EP | 0 867 183 A1 | 9/1998 | |
| EP | 0 901 786 A2 | 3/1999 | |
| EP | 1 027 886 | 8/2000 | |
| EP | 1 092 727 A2 | 4/2001 | |
| EP | 1 129 706 A2 | 9/2001 | |
| EP | 1 176 147 A1 | 1/2002 | |
| EP | 1 422 228 A1 | 5/2004 | |
| EP | 1 500 648 A1 | 1/2005 | |
| EP | 1 133 559 B1 | 8/2005 | |
| EP | 1 584 683 B1 | 7/2007 | |
| EP | 1 813 606 A1 | 8/2007 | |
| EP | 1 852 433 A1 | 11/2007 | |
| GB | 0 882 813 | 11/1961 | |
| GB | 1 422 263 A | 1/1976 | |
| JP | 25/27107 | 8/1996 | |
| JP | 11-116502 | 4/1999 | |
| JP | 2012-532124 | 12/2012 | |
| WO | WO-00/50562 A2 | 8/2000 | |
| WO | WO-02/098223 A1 | 5/2002 | |
| WO | WO-2004/037809 A1 | 5/2004 | |
| WO | WO-2004/078413 A1 | 9/2004 | |
| WO | WO-2004/089373 A1 | 10/2004 | |
| WO | WO-2004/113323 A1 | 12/2004 | |
| WO | WO-2005/011654 A2 | 2/2005 | |
| WO | WO-2005/061489 A1 | 7/2005 | |
| WO | WO-2005/061547 A2 | 7/2005 | |
| WO | WO-2005/082089 A2 | 9/2005 | |
| WO | WO-2005/121088 A1 | 12/2005 | |
| WO | WO-2006/054652 A1 | 5/2006 | |
| WO | WO-2006/074057 A2 | 7/2006 | |
| WO | WO-2006/076231 A2 | 7/2006 | |
| WO | WO-2006/091428 A2 | 8/2006 | |
| WO | WO-2006/124692 A2 | 11/2006 | |
| WO | WO-2006/133216 A2 | 12/2006 | |
| WO | WO-2006/134487 A1 | 12/2006 | |
| WO | WO-2007/003960 A1 | 1/2007 | |
| WO | WO-2007/003961 A2 | 1/2007 | |
| WO | WO-2007/023507 A2 | 3/2007 | |
| WO | WO-2007/035355 A2 | 3/2007 | |
| WO | WO-2007/039177 A2 | 4/2007 | |
| WO | WO 2007066189 A2 * | 6/2007 | A61K 9/1652 |
| WO | WO-2007/120702 A2 | 10/2007 | |
| WO | WO-2008/008887 A2 | 1/2008 | |
| WO | WO-2008/025800 A1 | 3/2008 | |
| WO | WO-2008/047201 A2 | 4/2008 | |
| WO | WO-2008/070692 A2 | 6/2008 | |
| WO | WO-2008/083238 A2 | 7/2008 | |
| WO | WO-2008/109702 A1 | 9/2008 | |
| WO | WO-2009/010429 | 1/2009 | |
| WO | WO-2009/010761 | 1/2009 | |
| WO | WO-2009/014637 | 1/2009 | |
| WO | WO-2009/016516 | 2/2009 | |
| WO | WO-2009/037394 | 3/2009 | |
| WO | WO-2009/070869 A1 | 6/2009 | |
| WO | WO-2010/008739 A2 | 1/2010 | |
| WO | WO-2010/013849 A1 | 2/2010 | |
| WO | WO-2010/048149 A2 | 4/2010 | |
| WO | WO-2011/041154 A1 | 4/2011 | |
| WO | WO-2010/029089 A2 | 3/2012 | |

OTHER PUBLICATIONS

U.S. Appl. No. 13/032,513, filed Feb. 22, 2011, Chen, et al.
U.S. Appl. No. 13/152,752, filed Jun. 3, 2011, Chen, et al.
U.S. Appl. No. 13/449,238, filed Apr. 17, 2012, Xin, et al.
U.S. Appl. No. 13/463,617, filed May 3, 2012, Jingyuan, et al.
U.S. Appl. No. 13/612,451, filed Sep. 12, 2012, Xin, et al.
Annoura, et al., "Synthesis and Biological Evaluation of New 4-Arlypiperidines and 4-Aryl-4-piperidinols: Dual Na+ and Ca2+ Channel Blockers with Reduced Affinity for Dopamine D2 Receptors," Biorganic & Medicinal Chemistry, 10, 2002, pp. 371-83.
Ashcroft & Gribble. "ATP-sensitive K+ Channels and Insulin Secretion: Their Role in Health and Disease," Diabetologia, (1999) 42: 903-19.
Barrett-Conner. "Epidemiology, Obesity, and Non-insulin-dependent Diabetes Mellitus" Epidemiologic Reviews, (1998) 11: 172-81.
Bell & Polonsky. "Diabetes Mellitus and Genetically Programmed Defects in β-cell Function," Nature, (2001) 414: 788-91.

(56) References Cited

OTHER PUBLICATIONS

Bighley et al., "Salt Forms of Drugs and Absorption," in Swarbrick, J. and Boylan, J.C., et al., eds. "Encyclopedia of Pharmaceutical Technology." 13 Ed., Marcel Dekker, NY (1996) pp. 453-499.
Blicklé. "Meglitinide Analogues: a Review of Clinical Data Focused on Recent Trials," Diabetes & Metabolism, (2006) 32(2): 113-20.
Blough, et al., "Synthesis and Transporter Binding Properties of 3.beta.-[4'(Phenylalkyl,—phenylalkenyl, and -phenylalkynl)phenyl]tropane-2.beta.-carboxylic Acid Methyl Esters: Evidence of a Remote Phenyl Binding Domain on the Dopamine Transporter," Journal of Medicinal Chemistry, 45:18, 2002, pp. 4029-4037.
Brubaker. "The Glucagon-Like Peptides Pleiotropic Regulators of Nutrient Homeostatsis," Annals of New York Academy of Sciences, (2006) 1070: 10-26.
Byrn et al., "Solid-State Chemistry of Drugs, 11: Hydrates and Solvates," 2nd ed., SSCI, Inc., (1999) 233-247 & 516.
Byrn, S.et al., Pharmaceutical Research, 1995, Vo I. 12, No. 7, p. 945-954.
Cantin et al., "PDE-10A Inhibitors as Insulin Secretagogues," Bioorganic & Medicinal Chemistry Letters, (2007) 17(10): 2869-73.
Castro, et al., "Enhancement of Oral Absorption in Selective 5-HT1D Receptor Agonists: Fluorinated 3[3-(Piperidin-1-yl)propyl]indoles," Journal of Medicinal Chemistry (1998) 41(15): 2667-70.
Cavaghan et al., "Interactions Between Insulin Resistance and Insulin Secretion in the Development of Glucose Intolerance," The Journal of Clinical Investigation, (2000) 106(3): 329-33.
Cavalla et al., "Analgetics Based on the Pyrrolidine Ring. V," Journal of Medicinal Chemistry, (1970) 13(5): 794-800.
Chiasson et al., "The Efficacy of Acarbose in the Treatment of Patients with Non-Insulin-dependent Diabetes Mellitus: A Multicenter Controlled Clinical Trial." Annals of Internal Medicine, (1994) 121(12): 928-35.
Chilean Examination Report dated Jun. 15, 2011 for Chilean Application No. 2042-2008.
Choi et al., "Alterations in Regulation of Energy Homeostasis in Cyclic Nucleotide Phosphodiesterase 3B-null Mice." Journal of Clinical Investigation, (2006) 116(12): 3240-51.
Coniff et al., "Acarbose: A Review of US Clinical Experience." Clinical Therapy, (1997) 19(1): 16-26.
Coniff et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus." American Journal of Medicine, (1995) 98: 443-51.
Crawley et al., "Methoxytetrahydropyrans. A New Series of Selective and Orally Potent 5-Lioxygenase Inhibitors," Journal of Medicinal Chemistry, (1992) 35(14): 2600-9.
Deacon. "Dipeptidyl Peptidase 4 Inhibition with Sitagliptin: a New Therapy for Type 2 Diabetes." Expert Opinion on Investigational Drugs, 16:4, 2007, pp. 533-545.
Deng et al., "A Novel and Efficient Synthesis of 2,5-Substituted 1,2,4-Triazol-3-Ones," Tetrahedron Letters, (2005) 46(46): 7993-6.
Drucker, "The Role of Gut Hormones in Glucose Homeostasis," Journal of Clinical Investigation, (2007) 117(1): 24-32.
Elahi et al., "The Insulinotropic Actions of Glucose-dependent Insulinotropic Polypeptide (GIP) and Glucagon-like Peptide-1 (7-37) in Normal and Diabetic Subjects," Regulatory Peptides, (1994) 61: 63-74.
Farilla et al., "Glucagon-Like Peptide 1 Inhibits Cell Apoptosis and Improves Glucose Responsiveness of Freshly Isolated Human Islets," Endocrinology, (2003) 144(12) 5149-58.
Farilla et al., "Glucagon-Like Peptide-1 Promotes Islet Cell Growth and Inhibits Apoptosis in Zucker Diabetic Rats," Endocrinology, 143:11, (2002), pp. 4397-4408.
Filipsson et al., "The Neuropeptide Pituitary Adenylate Cyclase-Activating Polypeptide and Islet Function," Diabetes, (2001) 50(9): 1959-69.
Flier, "Insulin receptors and insulin resistance," Annual Reviews of Medicine, 34, (1983), pp. 145-160.

Friedrichsen et al., "Stimulation of Pancreatic β-cell Replication by Incretins Involves Transcriptional Induction of Cyclin D1 via Multiple Signalling Pathways." Journal of Endocrinology, (2006) 188(3): 481-92.
Furman et al., "Modulation of Cyclic Nucleotides and Cyclic Nucleotide Phosphodiesterases in Pancreatic Islet β-cells and Intestinal L-cells as Targets for Treating Diabetes Mellitus," Current Opinions in Investigational Drugs, (2006) 7(10): 898-905.
Gavin, et al. "Report of the Expert Committee on the Diagnosis and Classification of Diabetes Mellitus", Diabetes Care, (2003) 26(Supp 1): S5-S20.
Gilon et al., "Mechanisms and Physiological Significance of the Cholinergic Control of Pancreatic β-Cell Function," Endocrinology Reviews, (2001) 22(5): 565-604.
Gloyn et al., "Insights into the Structure and Regulation of Glucokinase from a Novel Mutation (V62M), Which Causes Maturity-onset Diabetes of the Young." J Biol Chem (2005) 280(14): 14105-14113.
González et al., "Investigational treatments for type 2 diabetes mellitus: exenatide and liraglutide." Expert Opin Investig Drugs (2006) 15(8): 887-895.
Gould et al., "Pyrrolidines. IX. 3-Aryl-3-pyrrolidinols," Journal of Medicinal Chemistry, (1964) 7(1): 60-7.
Gould, P.L., "Salt Selection for Basic Drugs," International Journal Pharmaceutics, 33, 1986, pp. 201-217.
Green et al. "Dipeptidyl peptidase IV (DPP IV) inhibitors: a newly emerging drug class for the treatment of type 2 diabetes." Diabetes Vasc. Dis. Res. (2006), 3:159-165.
Greene, T.W., "Protective Groups in Organic Synthesis," 3rd Edition, John Wiley & Sons, Inc., (1999) 518-23.
Gromada et al., "Glucagon-Like Peptide 1(7-36) Amide Stimulates Exocytosis in Human Pancreatic beta-Cells by Both Proximal and Distal Regulatory Steps in Stimulus-Secretion Coupling." Diabetes (1998) 47(1): 57-65.
Guertin et al., "Small Molecule Glucokinase Activators as Glucose Lowering Agents: A New Paradigm for Diabetes Therapy." Curr Med Chem (2006) 13(15): 1839-1843.
Guillory, J.K., "Generation of Polymorphs, hydrates, Solvates and Amorphous Solids," in "Polymorphism in Pharmaceutical Solids." Brittain, H.G. ed., (1999) 183-220.
Haffner, "Management of Dyslipidemia in Adults With Diabetes." Diabetes Care (1998) 21(1): 160-178.
Han et al., "The Calcium/Calmodulin-dependent Phosphodiesterase PDE1C Down-regulates Glucose-induced Insulin Secretion." J Biol Chem (1999) 274(32): 22337-22344.
Hancock, B.C. et al., Journal of Pharmaceutical Sciences, 1997,vol. 86, No. 1, p. 1-12.
Hansen, "Towards Selective Kir6.2/SUR1 Potassium Channel Openers, Medicinal Chemistry and Therapeutic Perspectives." Curr Med Chem (2006) 13(4): 361-376.
Hansotia et al., "Extrapancreatic incretin receptors modulate glucose homeostasis, body weight, and energy expenditure." J Clin Invest (2007) 117(1): 143-152, Epub Dec. 21, 2006.
Härndahl et al., "Important Role of Phosphodiesterase 3B for the Stimulatory Action of cAMP on Pancreatic β-Cell Exocytosis and Release of Insulin." J Biol Chem (2002) 277(40): 37446-37455.
Hatakeyama et al., "Rapid glucose sensing by protein kinase A for insulin exocytosis in mouse pancreatic islets." J Physiol (2006) 570(Pt 2): 271-282.
Henquin, "Pathways in β-Cell Stimulus-Secretion Coupling as Targets from Therapeutic Insulin Secretagogues." Diabetes (2004) 53(Supp 3): S48-S58.
Holz, "Perspectives in Diabetes Epac: A New cAMP-Binding Protein in Support of Glucagon-Like Peptide-1 Receptor-Mediated Signal Transduction in the Pancreatic β-Cell." Diabetes (2004) 53(1): 5-13.
Hussain et al., "Increased Pancreatic β-Cell Proliferation Mediated by CREB Binding Protein Gene Activation." Mol Cell Biol (2006) 26(20): 7747-7759.
International Search Report and Written Opinion dated Feb. 22, 2010 in related PCT Application No. PCT/US2009/047551.
International Search Report and Written Opinion dated Jan. 26, 2009 in related PCT Application No. PCT/US2008/069714.

(56) References Cited

OTHER PUBLICATIONS

International Search Report and Written Opinion dated Jun. 19, 2009 in related PCT Application No. PCT/US2009/038847.
International Search Report and Written Opinion dated May 23, 2008 in related PCT Application No. PCT/US2007/088978.
International Search Report and Written Opinion dated Oct. 29, 2010 in related PCT Application No. PCT/US2010/049486.
International Search Report dated Oct. 10, 2011 in related PCT Application No. PCT/US2011/040972.
International Search Report dated Oct. 6, 2011 in related PCT Application No. PCT/US11/39069.
Iwamoto et al., "Effect of Combination Therapy of Troglitazone and Sulphonylureas in Patients with Type 2 Diabetes Who Were Poorly Controlled by Sulphonylurea Therapy Alone." Diabet Med (1996) 13: 365-370.
Kahn, "The Importance of β-Cell Failure in the Development and Progression of Type 2 Diabetes." J Clin Endicrinol Metab (2001) 86:4047-4058.
Kahn, "The Importance of the β-Cell in the Pathogenesis of Type 2 Diabetes Mellitus." Am J Med (2000) 108 Suppl 6a, 2S-8S.
Kahn, "Type 2 Diabetes: When Insulin Secretion Fails to Compensate for Insulin Resistance." Cell (1998) 92: 593-596.
Kaplan et al., "Cardiovascular diseases" in Health and Human Behavior, (McGraw-Hill, New York 1993): 206-242.
Kashima et al., "Critical Role of cAMP-GEFII Rim2 Complex in Incretin-potentiated Insulin Secretion." J Biol Chem (2001) 276(49): 46046-46053, Epub Oct. 11, 2001.
Kim et al., "(2R)-4-oxo-443-(trifluoromethyl)-5,6-dihydro[1,2,4]triazolo[4,3-a]pyrazin-7(8H)-yl]-1-(2,4,5-trifluorophenyl)butan-2-amine: A potent, orally active dipeptidyl peptidase IV inhibitor for the treatment of type 2 diabetes." J. Med. Chem., 2005, 48(1):141-151.
Kim et al., "Exendin-4 induction of cyclin D1 expression in INS-1 β-cells: involvement of cAMP-responsive element." J Endocrinol (2006) 188(3): 623-633.
Knowler et al., "Obesity in the Pima Indians: its magnitude and relationship with diabetes," Am. J. Clin. Nutr. (1991) 53:1543S-1551S.
Kwiterovich, "State-of-the-Art Update and Review: Clinical Trials of Lipid-Lowering Agents." Am J Cardiol (1998) 82(12A): 3U-17U.
Langer, "New Methods of Drug Delivery." Science (1990) 249: 1527-1533.
Le Bourdonnec, B., et al., "Discovery of a series of aminopiperidines as novel iNOS inhibitors," Bioorganic and Medicinal Chemistry Letters, vol. 18, Issue 1, pp. 336-343 (2008).
Le Bourdonnec, et al., "Synthesis and Structure-activity Relationships of a New Series of 2α-substitued Trans-4,5-dimethyl-4-(3-hydroxyphenyl)piperidine as µ-selective Opioid Antagonists," Bioorganic and Medicinal Chemistry Letters, (2006) 16(4): 864-8.
Levy et al., "Beta-cell Deterioration Determines the Onset and Rate of Progression of Secondary Dietary Failure in Type 2 Diabetes Mellitus: the 10-year Follow-up of the Belfast Diet Study." Diabetes Med (1998) 15: 290-296.
Li et al., "Glucagon-like Peptide-1 Receptor Signaling Modulates β Cell Apoptosis." J Biol Chem (2003) 278(1): 471-478.
Mahler et al., "Clinical Review 102 Type 2 Diabetes Mellitus: Update on Diagnosis, Pathophysiology, and Treatment." J Clin Endocrinol Metab (1999) 84(4): 1165-1171.
Matschinsky et al., "Perspectives in Diabetes the Network of Glucokinase-Expressing Cells in Glucose Homeostasis and the Potential of Glucokinase Activators for Diabetes Therapy." Diabetes (2006) 55(1): 1-12.
Matschinsky, "Glucokinase, Glucose Homeostasis, and Diabetes Mellitus." Curr Diab Rep (2005) 5(3): 171-176.
Meneilly et al., "The Effect of Glyburide on β-Cell Sensitivity to Glucose-Dependent Insulinotropic Polypeptide." Diabetes Care (1993) 16(1): 110-114.

Miura et al., "Glucagon-like peptide-1 induces a cAMP-dependent increase of [Na+]i associated with insulin secretion in pancreatic β-cells." Am J Physiol Endocrinol Metab (2003) 285, E1001-E1009.
Morissette, et al., "High-throughput Crystallization: Polymorphs, Salt, Co-crystals and Solvates of Pharmaceutical Solids," Advanced Drug Delivery Reviews, 56, 2004, pp. 275-300.
Nauck et al., "Preserved Incretin Activity of Glucagon-like Peptide 1 [7-36 Amide] but Not of Synthetic Human Gastric Inhibitory Polypeptide in Patients with type-2 Diabetes Mellitus." J Clin Invest (1993) 91: 301-307.
Office Action dated Sep. 14, 2012 in U.S. Appl. No. 13/000,868.
Prentki et al., "Islet β cell Failure in type 2 dieabetes." J Clin Invest (2006) 116(7): 1802-1812.
Qader et al., "Expression of islet inducible nitric oxide synthase and inhibition of glucose-stimulated insulin release after long-term lipid infusion in the rat is counteracted by PACAP27." Am J Physiol Endocrinol Metab (2007) 292(5): E1447-E1455.
Reaven, "Insulin Resistance and Human Disease: A Short History." J Basic & Clin Phys & Pharm (1998) 9: 387-406.
Reimann et al., "Signaling Mechanisms Underlying the Release of Glucagon-Like Peptide 1." Diabetes(2006) 55(Suppl 2): S78-S85.
Rendell, "The Role of Sulphonylureas in the Management of Type 2 Diabetes Mellitus." Drugs (2004) 64(12): 1339-13.58.
Saltiel, "New Perspectives into the Molecular Pathogenesis and Treatment of Type 2 Diabetes." Cell.(2001) 104: 517-529.
Sato, et al., "New µ-Opioid Receptor Agonists with Phenoxyacetic Acid Moiety," Chemical & Pharmaceutical Bulletin, (2002) 50(2): 292-7.
Saxena et al., "Genome-Wide Association Analysis Identifies Loci for Type 2 Diabetes and Triglyceride Levels." Science (2007) 316: 1331-1336.
Seino, "ATP-Sensitive Potassium Channels: A Model of Heteromultimeric Potassium Channel/Receptor Assemblies." Annu Rev Physiol (1999) 61: 337-362.
Shibasaki et al., "Interaction of ATP Sensor, cAMP Sensor, Ca2+ Sensor, and Voltage-dependent Ca2+ Channel in Insulin Granule Exocytosis." J Biol Chem (2004) 279(9): 7956-7961.
Singer, et al., "Synthesis of SAR of Tolylamine 5-HT6 Antagonists," Bioorganic & Medicinal Chemistry Letters, (2009) 19: 2409-12.
Soga et al., "Lysophosphatidylcholine Enhances Glucose-dependent Insulin Secretion via an Orphan G-protein-coupled Receptor." Biochemical and Biophysical Research Communications (2005) 326(4): 744-751.
Steinthorsdottir et al., "A Variant in CDKAL1 Influences Insulin Response and Risk of Type 2 Diabetes." Nature Genetics (2007) 39(6): 770-775.
Still et al., "Rapid Chromatographic Technique for Preparative Separations with Moderate Resolution." J. Org. Chem., 1978, 43(14):2923-2925.
Supplementary European Search Report dated Mar. 4, 2011 in related European Application No. 07869989.9.
Supplementary Partial European Search Report dated Jul. 25, 2012 in related European Application No. 09798422.3.
Thomas, et al., "Investigation of the N-Substituent Conformation Governing Potency and .mu. Receptor Subtype-Selectivity in (+)-(3R,4R)-Dimethyl-4-(3-hydroxyphenyl)-piperidine Opioid Antagonists," Journal of Medicinal Chemistry, 41:11, 1998, pp. 1980-1990.
Thorens et al., "Cloning and Functional Expression of the Human Islet GLP-1 Receptor: Demonstration that Exendin-4 is an Agonist and Exendin-(9-39) an Antagonist of the Receptor." Diabetes (1993) 42, 1678-1682.
Thorens, "GLUT2 in pancreatic and extra-pancreatic gluco-detection." Mol Membr Biol (2001) 18(4): 265-273.
Turner et al., "Glycemic Control With Diet, Sulfonylurea, Metformin, or Insulin in Patients With Type 2 Diabetes Mellitus: Progressive Requirement for Multiple Therapies (UKPDS 49)." JAMA (1999) 281(21): 2005-2012.
Turner et al., "Insulin resistance, impaired glucose tolerance and non-insulin-dependent diabetes, pathologic mechanisms and treatment: Current status and therapeutic possibilities." Prog Drug Res (1998) 51: 33-94.

(56) References Cited

OTHER PUBLICATIONS

U.K. Prospective Diabetes Study Group: "UKPDS 28: A Randomized Trial of Efficacy of Early Addition of Metformin in Sulfonylurea-Treated Type 2 Diabetes," Diabetes Care (1998) 21(1): 87-92.
U.S. Notice of Allowance dated Sep. 18, 2015.
U.S. Office Action dated May 18, 2015.
U.S. Office Action on dated Sep. 10, 2014.
Vilsbøll et al., "Reduced Postprandial Concentrations of Intact Biologically Active Glucagon-Like Peptide 1 in Type 2 Diabetic Patients." Diabetes (2001) 50: 609-613.
Vippagunta, et al., "Crystalline Solids," Advanced Drug Delivery Reviews, (2001) 48: 3-26.
Waid, et al., "Constrained Amino Acids, An Approach to the Synthesis of 3-Substituted Prolines," Tetrahedron Letters, (1996) 37(24): 4091-4.
Walz et al., "Early and rapid development of insulin resistance, islet dysfunction and glucose intolerance after high-fat feeding in mice overexpressing phosphodiesterase 3B." J Endocrinol (2006) 189(3): 629-641.
Wu, et al., "Pyrrolidines. VII. 3-Hydroxy-1-Pyrrolidinecarboxylic Acid Esters," Journal of Medicinal Chemistry, 5:4, 1962, pp. 752-762.
Yamada et al., "Cytosolic Ca2+ responses to sub-picomolar and nanomolar PACAP in pancreatic β-cells are mediated by VPAC2 and PAC1 receptors." Regul Pept (2004) 123(1-3): 147-153.
Zhou et al., "Overexpression of Repressive cAMP Response Element Modulators in High Glucose and Fatty Acid-treated Rat Islets." J Biol Chem (2003) 278(51): 51316-51323.

* cited by examiner

Non-Sink Dissolution Profile for Compound A Melt Extruded Compositions Tested in Simulated Gastric Fluid Non-Sink Dissolution Profile for Compound A Melt Extruded Compositions Tested in Simulated Fed State Intestinal Fluid Non-Sink Dissolution Profile for Compound A Melt Extruded Compositions Tested in Simulated Fasted State Intestinal Fluid

Process Flow Chart for Manufacture of 25% Compound A:CAP SDD

Residual Acetone Content as a Function of Tray-Drying Time at 40°C/30% RH for 25% Compound A:CAP SDD, based on Headspace Gas Chromatography (GC) Analysis

*In vitro* Dissolution Results for 25% Compound A:CAP SDD and Crystalline Compound A

Process Flow Chart for Manufacture of Uncoated Compound A SDD 25 mg Tablets

Process Flow Chart for Manufacture of Uncoated Compound A SDD 100 mg Tablets

Process Flow Chart for Film Coating of Uncoated Compound A SDD 25
and 100 mg Tablets Mean ± SE Concentration-Time Profile after Administration of Repeat (5) Daily Doses
of Compound A to Subjects with IFG Mean Compound A Single Dose PK Parameters: Comparison of Microcrystalline and SDD Formulation AUC Compound A Single Dose PK Parameters: Comparison of Microcrystalline and SDD Formulation $C_{max}$

Figure 13

Mean ± SE Percent Reduction in Glucose Excursion During a MMTT After
Administration of Repeat (4) Daily Doses of Compound A to Subjects with Pre-Diabetes

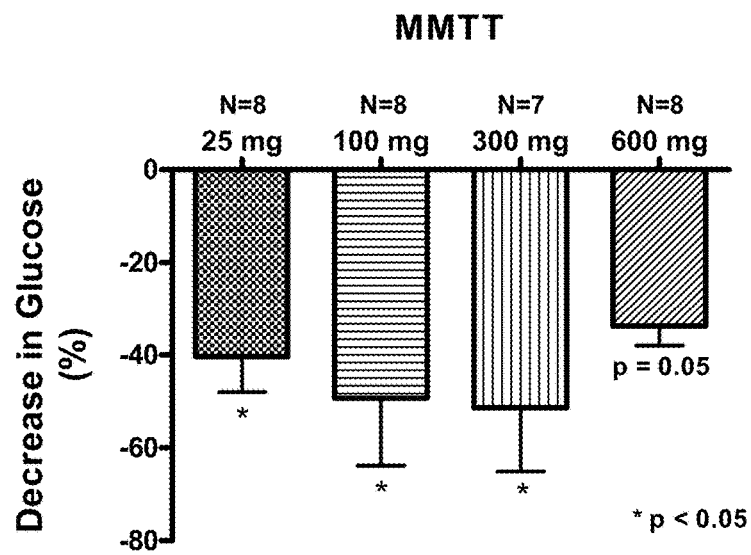

Figure 14

Mean ± SE Percent Reduction in Glucose Excursion During a MMTT After
Administration of Repeat (4) Daily Doses of Compound A in Pooled Subsets of Subjects
with Increasing Degrees of Glucose Intolerance at Baseline

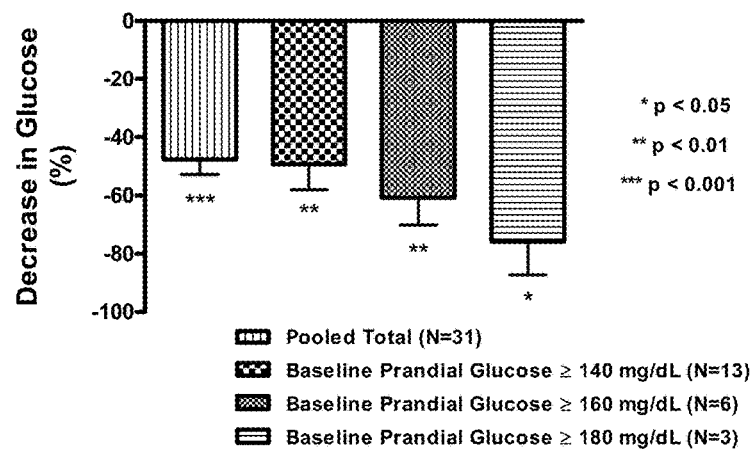

COMPOSITIONS OF 5-ETHYL-2-{4-[4-(4-TETRAZOL-1-YL-PHENOXYMETHYL)-THIAZOL-2-YL]-PIPERIDIN-1-YL}-PYRIMIDINE

CROSS-REFERENCE TO RELATED APPLICATION

This application is a continuation of U.S. patent application Ser. No. 13/165,651, filed Jun. 21, 2011 (now U.S. Pat. No. 9,241,924, issued Jan. 26, 2016), which claims the benefit of U.S. Provisional Patent Application Ser. No. 61/357,981, filed on Jun. 23, 2010, both of which are incorporated herein by reference in their entirety.

FIELD OF THE INVENTION

This invention relates to the field of pharmaceutical chemistry and, more specifically, to pharmaceutical formulations as well as to intermediates used to prepare such formulations and to methods for manufacturing such formulations.

BACKGROUND OF THE INVENTION

Pyrimidine compounds useful for treatment of diabetes and other metabolic disorders are disclosed in U.S. Pat. No. 7,638,541 which is incorporated herein by reference in its entirety. One such compound is 5-ethyl-2-{4-[4-(4-tetrazol-1-yl-phenoxymethyl)-thiazol-2-yl]-piperidin-1-yl}-pyrimidine. Methods for preparing this compound are set forth in U.S. Ser. No. 61/351,803 filed on Jun. 4, 2010 which application is incorporated in its entirety by reference. This compound is an agonist of GPR119, a GPCR that is expressed in the pancreatic islets and the gastrointestinal tract. GPR agonists have been shown to stimulate glucose-dependent insulin secretion and release of incretin hormones leading to a preservation of beta cell health.

Heretofore, described formulations of 5-ethyl-2-{4-[4-(4-tetrazol-1-yl-phenoxymethyl)-thiazol-2-yl]-piperidin-1-yl}-pyrimidine possessed less than optimal bioavailability properties. In turn, increased bioavailability of 5-ethyl-2-{4-[4-(4-tetrazol-1-yl-phenoxymethyl)-thiazol-2-yl]-piperidin-1-yl}-pyrimidine.

SUMMARY OF THE INVENTION

This invention provides pharmaceutical formulations comprising a pharmaceutically inert carrier and a therapeutically effective amount of 5-ethyl-2-{4-[4-(4-tetrazol-1-yl-phenoxymethyl)-thiazol-2-yl]-piperidin-1-yl}-pyrimidine. The pharmaceutical formulations disclosed herein exhibit improved solubility and pharmacokinetic profile.

BRIEF DESCRIPTION OF THE DRAWINGS

FIG. 13 provides a graphical representation of the percent reduction in glucose excursion during a MITT after administration of repeat (4) daily doses of Compound A to subjects with pre-diabetes.

FIG. 14 provides the Percent Reduction in glucose excursion during a MITT after administration of repeat (4) daily doses of Compound A in pooled subsets of subjects with increasing degrees of glucose intolerance at baseline.

DETAILED DESCRIPTION OF THE INVENTION

Figure 1:
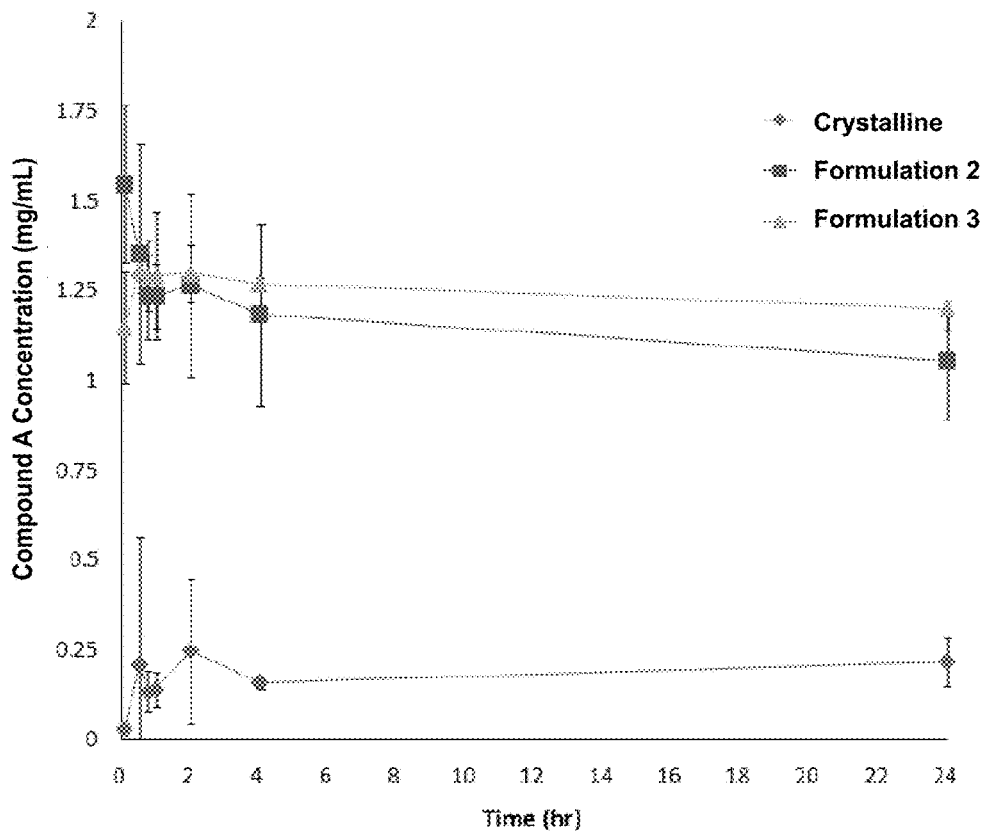
FIG. 1 provides a non-sink dissolution profile for compound A melt extruded compositions tested in simulated gastric fluid.

The invention is directed to a pharmaceutical formulation comprising a pharmaceutically inert carrier and a therapeutically effective amount of 5-ethyl-2-{4-[4-(4-tetrazol-1-yl-phenoxymethyl)-thiazol-2-yl]-piperidin-1-yl}-pyrimidine

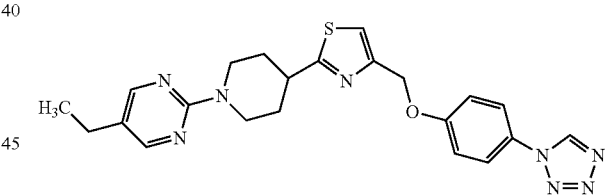

wherein at least a portion of the 5-ethyl-2-{4-[4-(4-tetrazol-1-yl-phenoxymethyl)-thiazol-2-yl]-piperidin-1-yl}-pyrimidine. However, prior to describing this invention in greater detail, the following terms will first be defined.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an", and "the" include plural referents unless the context clearly dictates otherwise. Thus, for example, reference to "a pharmaceutically inert carrier" includes a plurality of such carriers.

Definitions

Unless defined otherwise, all technical and scientific terms used herein have the same meaning as commonly understood by one of ordinary skill in the art to which this invention belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "about" when used before a numerical designation, e.g., temperature, time, amount, and concentration, including range, indicates approximations which may vary by (+) or (−) 10%, 5% or 1%.

As used herein, the term "Compound A" refers to 5-ethyl-2-{4-[4-(4-tetrazol-1-yl-phenoxymethyl)-thiazol-2-yl]-piperidin-1-yl}-pyrimidine

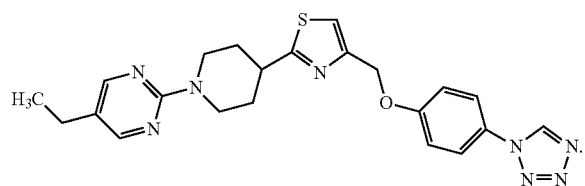 [SMILES: CCc1cnc(N2CCC(c3nc(COc4ccc(-n5cnnn5)cc4)cs3)CC2)nc1]

As used herein, the term "crystalline" refers to solid 5-ethyl-2-{4-[4-(4-tetrazol-1-yl-phenoxymethyl)-thiazol-2-yl]-piperidin-1-yl}-pyrimidine, wherein the solid exhibits long-range order in three dimensions of at least about 100 repeat units in each dimension.

As used herein, the term "non-crystalline" refers to solid 5-ethyl-2-{4-[4-(4-tetrazol-1-yl-phenoxymethyl)-thiazol-2-yl]-piperidin-1-yl}-pyrimidine, that does not exhibit any long range order in the positions of the atoms. Thus, the term non-crystalline is intended to include not only solid which has essentially no order, but also solid which may have some small degree of order, but the order is in less than three dimensions and/or is only over short distances. Non-crystalline compound may be characterized by techniques known in the art such as powder x-ray diffraction (PXRD) crystallography, solid state NMR, or thermal techniques such as differential scanning calorimetry (DSC).

As used herein, the term "solid dispersion" refers to a dispersion in which at least a portion of the 5-ethyl-2-{4-[4-(4-tetrazol-1-yl-phenoxymethyl)-thiazol-2-yl]-piperidin-1-yl}-pyrimidine, is non-crystalline and dispersed in a water soluble, biologically compatible polymer. The solid dispersions of the invention can be prepared by methods known in the art, including, but not limited to, solid dispersions formed by mechanical, thermal and solvent processes. Exemplary mechanical processes include milling and extrusion; melt processes, such as high temperature fusion, solvent-modified fusion and melt-congeal processes; and solvent processes, such as non-solvent precipitation, spray coating and spray drying. See, for example, the following U.S. patents, the pertinent disclosures of which are incorporated herein by reference: U.S. Pat. Nos. 5,456,923 and 5,939,099, which describe forming dispersions by extrusion processes; U.S. Pat. Nos. 5,340,591 and 4,673,564, which describe forming dispersions by milling processes; and U.S. Pat. Nos. 5,707,646 and 4,894,235, which describe forming dispersions by melt congeal processes. In one embodiment, the solid dispersion is formed by spray drying, as disclosed in European Patent Application Publication No. 0 901 786 A2. In this process, the 5-ethyl-2-{4-[4-(4-tetrazol-1-yl-phenoxymethyl)-thiazol-2-yl]-piperidin-1-yl}-pyrimidine with or without the water soluble, biologically compatible polymer are dissolved in a suitable solvent, such as acetone, acetonitrile, methanol, ethanol, and methylethylketone, and the solvent is then rapidly removed from the solution by spray drying to form the solid dispersion. An example of a solid dispersion of this invention is the spray-dried solid dispersion comprising about 25 weight percent of Compound A substantially homogenously intermixed with a water soluble, biologically compatible polymer.

As used herein, the term "pharmaceutically inert carrier" refers to carriers which are inert, in the sense that they do not chemically react with 5-ethyl-2-{4-[4-(4-tetrazol-1-yl-phenoxymethyl)-thiazol-2-yl]-piperidin-1-yl}-pyrimidine in an adverse manner, are pharmaceutically acceptable, and have at least some solubility in aqueous solution at physiologically relevant pHs (e.g. pH1-8). Examples of pharmaceutically inert carriers are well known in the literature and, include by way of example only, cellulose acetate phthalate, magnesium stearate, lactose, lactose monohydrate, crospovidone, microcrystalline cellulose, colloidal silica dioxide, and the like.

As used herein, the phrase "water soluble, biologically compatible polymer" refers to polymers which do not interact with 5-ethyl-2-{4-[4-(4-tetrazol-1-yl-phenoxymethyl)-thiazol-2-yl]-piperidin-1-yl}-pyrimidine in an adverse manner that is detrimental to its use in vivo, are pharmaceutically acceptable, have at least some solubility in aqueous solution at physiologically relevant pHs (e.g. pH1-8) and which, when combined with Compound A to form a solid dispersion as that term is defined above, impart enhanced solubility to Compound A. The water soluble, biologically compatible polymer can be neutral or ionizable, and have an aqueous-solubility of at least 0.1 mg/mL over at least a portion of the pH range of 1 to 8. In one embodiment, the glass-transition temperature (Tg) of the polymer is great enough so that the resulting solid dispersion has a relatively high Tg (greater than 50° C. at 50% relative humidity (RH)). The polymer may have a Tg of at least 100° C. at 50% RH, at least 105° C. at 50% RH, or even at least 110° C. at 50% RH.

As used herein, the term "substantially homogeneous" refers to solid dispersions as defined above wherein Compound A is dispersed in the solid dispersion such that the concentration of Compound A in any given amount of the solid dispersion is substantially uniform to that of any other given amount of the solid dispersion.

As used herein, the phrase "therapeutically effective amount" means the amount of 5-ethyl-2-{4-[4-(4-tetrazol-1-yl-phenoxymethyl)-thiazol-2-yl]-piperidin-1-yl}-pyrimidine that will elicit the biological or medical response of a tissue, system, animal or human that is being sought by the attending clinician. "A therapeutically effective amount" includes the amount of 5-ethyl-2-{4-[4-(4-tetrazol-1-yl-phenoxymethyl)-thiazol-2-yl]-piperidin-1-yl}-pyrimidine that, when administered to a mammal for treating a disease, is sufficient to effect such treatment for the disease. The "therapeutically effective amount" will vary depending on the pharmaceutically inert carrier, the disease and its severity and the age, weight, etc., of the mammal to be treated.

This invention is predicated in part on the discovery that the water solubility and the bioavailability of 5-ethyl-2-{4-[4-(4-tetrazol-1-yl-phenoxymethyl)-thiazol-2-yl]-piperidin-1-yl}-pyrimidine is enhanced when at least a portion (e.g., more than 25%) of the compound is non-crystalline and preferably employed in combination with a water soluble, biologically compatible polymer. Without being limited to any theory, it is believed that the water soluble, biologically compatible polymer assists in maintaining the non-crystallinity of this compound. Accordingly, the invention is directed to a pharmaceutical formulation comprising a pharmaceutically inert carrier, and a therapeutically effective amount of 5-ethyl-2-{4-[4-(4-tetrazol-1-yl-phenoxymethyl)-thiazol-2-yl]-piperidin-1-yl}-pyrimidine

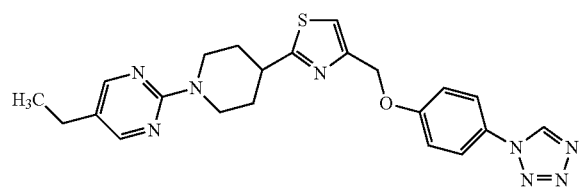 [SMILES: CCc1cnc(N2CCC(c3nc(COc4ccc(-n5cnnn5)cc4)cs3)CC2)nc1]

wherein at least a portion of said 5-ethyl-2-{4-[4-(4-tetrazol-1-yl-phenoxymethyl)-thiazol-2-yl]-piperidin-1-yl}-pyrimidine is non-crystalline.

This invention is further directed to intermediates useful in this invention wherein said intermediate is a solid dispersion comprising a water soluble, biologically compatible polymer 5-ethyl-2-{4-[4-(4-tetrazol-1-yl-phenoxymethyl)-thiazol-2-yl]-piperidin-1-yl}-pyrimidine wherein at least a portion of said 5-ethyl-2-{4-[4-(4-tetrazol-1-yl-phenoxymethyl)-thiazol-2-yl]-piperidin-1-yl}-pyrimidine is non-crystalline.

Formulations

In one aspect provided is a pharmaceutical formulation comprising a pharmaceutically inert carrier and 5-ethyl-2-{4-[4-(4-tetrazol-1-yl-phenoxymethyl)-thiazol-2-yl]-piperidin-1-yl}-pyrimidine

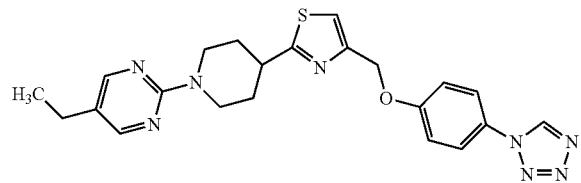 [SMILES: CCc1cnc(N2CCC(c3nc(COc4ccc(-n5cnnn5)cc4)cs3)CC2)nc1]

wherein from about 25% to about 100%, by weight, of the 5-ethyl-2-{4-[4-(4-tetrazol-1-yl-phenoxymethyl)-thiazol-2-yl]-piperidin-1-yl}-pyrimidine is non-crystalline and is contained within a solid dispersion which further comprises a water soluble, biologically compatible polymer.

In some embodiments, from about 50% to about 100%, by weight, of the 5-ethyl-2-{4-[4-(4-tetrazol-1-yl-phenoxymethyl)-thiazol-2-yl]-piperidin-1-yl}-pyrimidine is non-crystalline. In some embodiments, from about 75% to about 100%, by weight, of the 5-ethyl-2-{4-[4-(4-tetrazol-1-yl-phenoxymethyl)-thiazol-2-yl]-piperidin-1-yl}-pyrimidine is non-crystalline. In some embodiments, about 95%, by weight, of the 5-ethyl-2-{4-[4-(4-tetrazol-1-yl-phenoxymethyl)-thiazol-2-yl]-piperidin-1-yl}-pyrimidine is non-crystalline.

In some embodiments, the invention further comprises solid dispersions of 5-ethyl-2-{4-[4-(4-tetrazol-1-yl-phenoxymethyl)-thiazol-2-yl]-piperidin-1-yl}-pyrimidine substantially homogenously dispersed throughout the solid dispersion wherein the solid dispersion further comprises a water soluble, biologically compatible polymer. Water soluble, biologically compatible polymers suitable for use in the pharmaceutical formulations of the present invention may be cellulosic or non-cellulosic. In certain embodiments, the polymers are neutral or ionizable in aqueous solution. Of these, ionizable and cellulosic polymers are preferred, with ionizable cellulosic polymers being more preferred.

Exemplary water-soluble polymers include hydroxypropyl methyl cellulose acetate succinate, hydroxypropyl methyl cellulose, hydroxypropyl methyl cellulose phthalate, carboxy methyl ethyl cellulose, cellulose acetate phthalate, cellulose acetate trimellitate, and mixtures thereof.

In some embodiments, said water soluble polymer is selected from the group consisting of povidone, copovidone, hypromellose acetate succinate, polyethylene glycol, hydroxypropyl methyl cellulose acetate succinate, hydroxypropyl methyl cellulose, hydroxypropyl methyl cellulose phthalate, carboxy methyl ethyl cellulose, cellulose acetate trimellitate and cellulose acetate phthalate.

In some embodiments, said water soluble, biologically compatible polymer is selected from the group consisting of hydroxypropyl methyl cellulose acetate succinate, hydroxypropyl methyl cellulose, hydroxypropyl methyl cellulose phthalate, carboxy methyl ethyl cellulose, cellulose acetate trimellitate and cellulose acetate phthalate. In some embodiments, said polymer is cellulose acetate phthalate.

In some embodiments, the solid dispersion comprises from about 5% to about 75%, by weight, of 5-ethyl-2-{4-[4-(4-tetrazol-1-yl-phenoxymethyl)-thiazol-2-yl]-piperidin-1-yl}-pyrimidine.

In some embodiments, the solid dispersion is employed to provide for pharmaceutical formulations further comprising a pharmaceutically inert carrier wherein the formulation comprises from about 10% to about 50%, by weight, of 5-ethyl-2-{4-[4-(4-tetrazol-1-yl-phenoxymethyl)-thiazol-2-yl]-piperidin-1-yl}-pyrimidine.

In some embodiments, the pharmaceutical formulation comprises from about 20% to about 30%, by weight, of 5-ethyl-2-{4-[4-(4-tetrazol-1-yl-phenoxymethyl)-thiazol-2-yl]-piperidin-1-yl}-pyrimidine.

In some embodiments, the pharmaceutical formulation comprises about 5%, by weight, of 5-ethyl-2-{4-[4-(4-tetrazol-1-yl-phenoxymethyl)-thiazol-2-yl]-piperidin-1-yl}-pyrimidine, or alternatively, about 10% by weight, or about 15% by weight, or about 20% by weight, or about 25% by weight, or about 30% by weight, or about 35% by weight, or about 40% by weight, or about 45% by weight, or about 50% by weight, or about 55% by weight, or about 60% by weight, or about 65% by weight, or about 70% by weight, or about 75% by weight, or about 80% by weight, or about 85% by weight, or about 90% by weight, or about 95% by weight.

In some embodiments, the 5-ethyl-2-{4-[4-(4-tetrazol-1-yl-phenoxymethyl)-thiazol-2-yl]-piperidin-1-yl}-pyrimidine can exist within the solid dispersion in relatively pure non-crystalline domains, or, in some embodiments, is distributed substantially homogeneously throughout the solid dispersion.

In some embodiments, the solid dispersions of this invention are substantially homogenous and comprising a water soluble, biologically compatible polymer and a therapeutically effective amount of 5-ethyl-2-{4-[4-(4-tetrazol-1-ylphenoxymethyl)-thiazol-2-yl]-piperidin-1-yl}-pyrimidine. In certain embodiments, the fraction of 5-ethyl-2-{4-[4-(4-tetrazol-1-yl-phenoxymethyl)-thiazol-2-yl]-piperidin-1-yl}-pyrimidine that is present in relatively pure non-crystalline domains or regions within the solid dispersion is relatively small, on the order of less than 20% by weight, and preferably less than 10% by weight of the total amount of 5-ethyl-2-{4-[4-(4-tetrazol-1-yl-phenoxymethyl)-thiazol-2-yl]-piperidin-1-yl}-pyrimidine in the composition.

In one of its method aspects, the invention is directed to a method of producing solid dispersions comprising a therapeutically effective amount of 5-ethyl-2-{4-[4-(4-tetrazol-1-yl-phenoxymethyl)-thiazol-2-yl]-piperidin-1-yl}-pyrimidine and a water soluble, biologically compatible polymer, wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline, which method comprises the steps of:

a) combining 5-ethyl-2-{4-[4-(4-tetrazol-1-yl-phenoxymethyl)-thiazol-2-yl]-piperidin-1-yl}-pyrimidine and a solvent to form solution A;

b) further combining the water soluble, biologically compatible polymer;

c) rapidly removing the solvent from solution A.

In some embodiments, the non-crystalline form of 5-ethyl-2-{4-[4-(4-tetrazol-1-yl-phenoxymethyl)-thiazol-2-yl]-piperidin-1-yl}-pyrimidine can be prepared by combining crystalline 5-ethyl-2-{4-[4-(4-tetrazol-1-yl-phenoxymethyl)-thiazol-2-yl]-piperidin-1-yl}-pyrimidine with a solvent to form solution C and rapidly removing solution C. The non-crystalline form of 5-ethyl-2-{4-[4-(4-tetrazol-1-yl-phenoxymethyl)-thiazol-2-yl]-piperidin-1-yl}-pyrimidine can then be used to form the solid dispersions described herein.

In another of its method aspects, the present invention is directed to a method of producing solid dispersions wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline, which method comprises the steps of:

a) combining non-crystalline 5-ethyl-2-{4-[4-(4-tetrazol-1-yl-phenoxymethyl)-thiazol-2-yl]-piperidin-1-yl}-pyrimidine and a solvent to form solution A;

b) combining solution A and a water soluble, biologically compatible polymer to form solution B; and c) rapidly removing the solvent from solution B.

In some embodiments, the 5-ethyl-2-{4-[4-(4-tetrazol-1-yl-phenoxymethyl)-thiazol-2-yl]-piperidin-1-yl}-pyrimidine step a) is crystalline. However, in one embodiment, the non-crystalline form of this compound can be used.

It is contemplated that any suitable water soluble, biologically compatible polymer can be used in step b). Non-limiting examples include, hydroxypropyl methyl cellulose acetate succinate, hydroxypropyl methyl cellulose, hydroxypropyl methyl cellulose phthalate, carboxy methyl ethyl cellulose, cellulose acetate phthalate, cellulose acetate trimellitate and cellulose acetate phthalate. In one embodiment, the water soluble, biologically compatible polymer is cellulose acetate phthalate.

In some embodiments, the step of rapidly removing the solvent from solution B employs a spray-dryer. A spray dryer combines a liquid stream (e.g., solution A or B, above) with a drying gas, and separates the solute or suspension as a solid and the solvent into a vapor. The solid can be collected in a drum or cyclone. The liquid input stream is sprayed through a nozzle into a hot vapor stream and vaporized. Solids form as moisture quickly leaves the droplets. A nozzle is usually used to make the droplets as small as possible, maximising heat transfer and the rate of water vaporization. When a flammable solvent is used, oxygen is normally excluded from all parts of the spray drying apparatus. Therefore, suitable drying gases for use in the methods disclosed herein include inert gases, such as nitrogen, argon, carbon dioxide, helium, krypton, and xenon, at a flow rate of about 1200 g/min to about 2500 g/min. In some embodiments, the flow rate is about 1850 g/min. Typical droplet sizes can range from about 1 to about 500 micrometers, depending on the nozzle selected. Accordingly, in some embodiments, the smallest diameter of the solid dispersion is from about 1 to about 500 micrometers, or from about 1 to about 400 micrometers, or from about 5 to about 300 micrometers, or from about 5 to about 200 micrometers, or from about or 5 to about 100 micrometers, or from about or 5 to about 80 micrometers, or from about or 5 to about 60 micrometers, or from about or 5 to about 40 micrometers, or from about or 5 to about 50 micrometers, or from about or 10 to about 40 micrometers, or from about or 15 to about 35 micrometers, or about 25 micrometers.

In some embodiments, solution B is delivered to the spray-dryer at a rate of from about 175 grams/min to about 250 g/min. In some embodiments, solution B is delivered to the spray-dryer at a rate of from about 200 grams/min to about 230 g/min. In some embodiments, solution B is delivered to the spray-dryer at a pressure of from about 150 psi to about 500 psi. In some embodiments, solution B is delivered to the spray-dryer at a pressure of from about 200 psi to about 450 psi. In some embodiments, solution B is delivered to the spray-dryer at a pressure of from about 300 psi to about 315 psi. For commercial scale manufacturing, the drying gas flow rate can be significantly higher. The above provides for rapid removal of the solvent such that at least a portion of Compound A remains non-crystalline.

Suitable solvents for use in the spray-dryer include polar organic solvents, such as alcohols such as methanol, ethanol, n-propanol, isopropanol, and butanol; ketones such as acetone, methyl ethyl ketone and methyl isobutyl ketone; esters such as ethyl acetate and propyl acetate; and various other solvents, such as tetrahydrofuran, acetonitrile, methylene chloride, toluene, and 1,1,1-trichloroethane. In some embodiments, the solvent of solution A is acetone.

The temperature of the spray-dryer can be adjusted based on the solvent employed and the size of the nozzle. In some embodiments, the spray drying is performed at a temperature of between about 100° C. and about 150° C. In some embodiments, the spray drying is performed at a temperature of between about 115° C. and about 135° C. In some embodiments, the spray drying is performed at a temperature of about 125° C.

In some embodiments, the solid dispersions of this invention can be prepared by hot melting the water-soluble, biologically compatible polymer, adding the desired amount of 5-ethyl-2-{4-[4-(4-tetrazol-1-yl-phenoxymethyl)-thiazol-2-yl]-piperidin-1-yl}-pyrimidine to the hot melt under conditions to provide a uniform dispersion of the hot melt and then extruding the hot melt to form a solid dispersionsolid dispersion. The solid dispersion produced herein is sometimes referred to as a "hot melt extrudate". Suitable polymers for hot melt purposes include, for example, povidone, copovidone, hypromellose acetate succinate, and polyethylene glycol.

Compounds of the Invention

The pharmaceutical formulations of the present invention comprise a therapeutically effective amount of 5-ethyl-2-{4-[4-(4-tetrazol-1-yl-phenoxymethyl)-thiazol-2-yl]-piperidin- 1-yl}-pyrimidine, collectively referred to herein a "compound A". Methods for the preparation of the compound A are disclosed in U.S. Ser. No. 61/351,803 filed on Jun. 4, 2010 which application is incorporated in its entirety by reference. Exemplary methods for the preparation of 5-ethyl-2-{4-[4-(4-tetrazol-1-yl-phenoxymethyl)-thiazol-2-yl]-piperidin-1-yl}-pyrimidine for use in the pharmaceutical formulations disclosed herein are detailed herein below.

In one embodiment, provided is a method for preparing 5-ethyl-2-{4-[4-(4-tetrazol-1-yl-phenoxymethyl)-thiazol-2-yl]-piperidin-1-yl}-pyrimidine

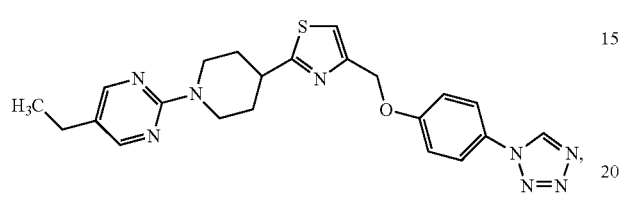

the method comprising:

(a) contacting a compound of Formula (I) with di-tert-butyl dicarbonate (Boc₂O) to form a compound of Formula (II)

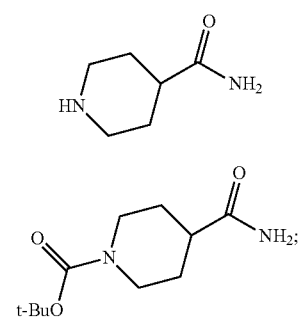

(b) contacting the compound of Formula (II) with a compound of Formula (III) to form a compound of Formula (IV)

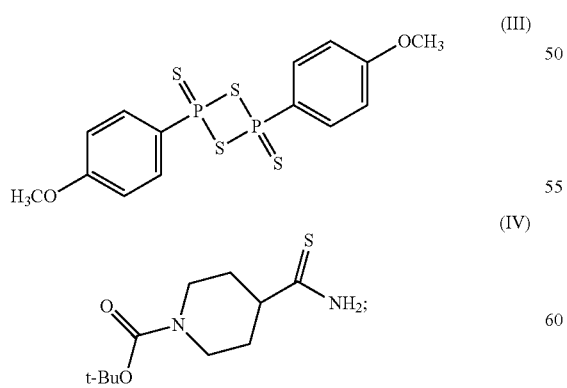

(c) contacting the compound of Formula (IV) with a compound of Formula (V) to form a compound of Formula (VI)

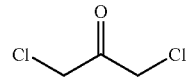

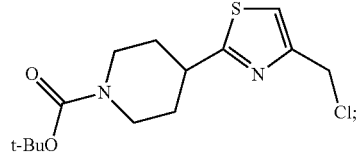

(d) contacting the compound of Formula (VI) with a compound of Formula (VII) to form a compound of Formula (VIII)

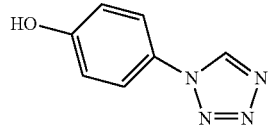

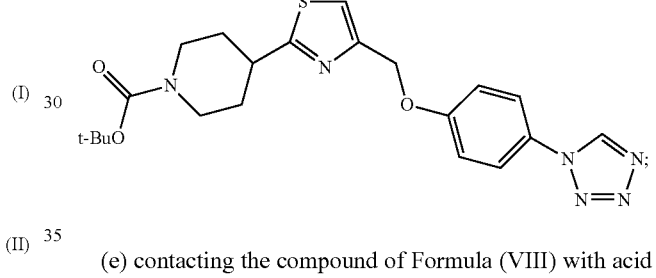

(e) contacting the compound of Formula (VIII) with acid to form a compound of Formula (IX)

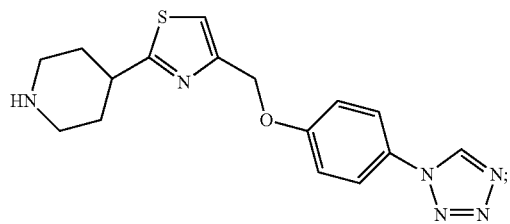

(f) contacting in dimethylformamide in presence of base the compound of Formula (IX) with a compound of Formula (X) wherein L is a leaving group such as F, Cl, Br, I, OS(O)₂CF₃, OS(O)₂CH₃ and OS(O)CF₃

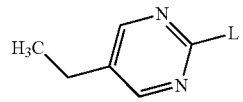

to form 5-ethyl-2-{4-[4-(4-tetrazol-1-yl-phenoxymethyl)-thiazol-2-yl]-piperidin-1-yl}-pyrimidine.

In one embodiment, provided is method for preparing 5-ethyl-2-{4-[4-(4-tetrazol-1-yl-phenoxymethyl)-thiazol-2-yl]-piperidin-1-yl}-pyrimidine

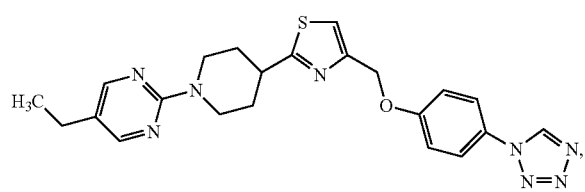 [SMILES: CCc1cnc(N2CCC(c3nc(COc4ccc(-n5cnnn5)cc4)cs3)CC2)nc1]

comprising contacting a compound of Formula (XXIV) with a compound of Formula (VII) in presence of base, such as NaOH, Na$_2$CO$_3$, K$_2$CO$_3$, Cs$_2$CO$_3$ and NaH

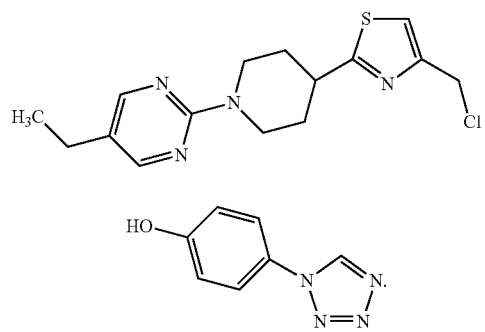
(XXIV)

(VII)

In one embodiment, provided is a method for preparing 5-ethyl-2-{4-[4-(4-tetrazol-1-yl-phenoxymethyl)-thiazol-2-yl]-piperidin-1-yl}-pyrimidine

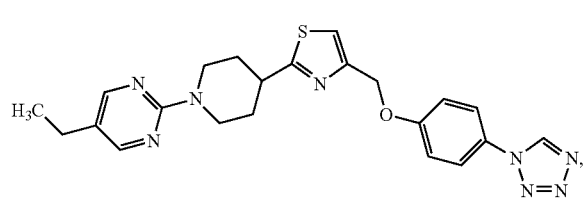 [SMILES: CCc1cnc(N2CCC(c3nc(COc4ccc(-n5cnnn5)cc4)cs3)CC2)nc1]

the method comprising:

(a) contacting a compound of Formula (I) with a compound of Formula (XXI) wherein T is a leaving group such as F, Cl, Br, I, OS(O)$_2$CF$_3$, OS(O)$_2$CH$_3$ and OS(O)CF$_3$ to form a compound of Formula (XXII)

(I)

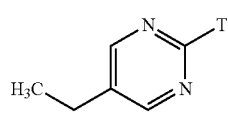

(XXI)

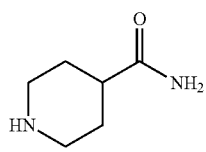

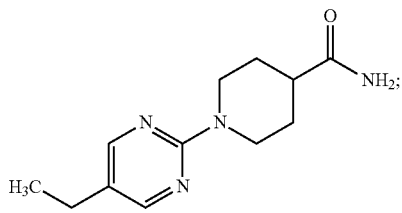
(XXII)

(b) contacting the compound of Formula (XXII) with a compound of Formula (III) to form a compound of Formula (XXIII)

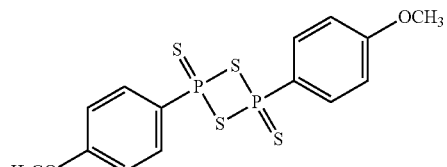
(III)

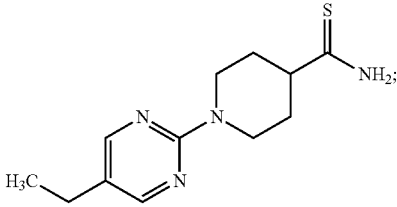
(XXIII)

(c) contacting the compound of Formula (XXIII) with a compound of Formula (V) to form a compound of Formula (XXIV)

(V)

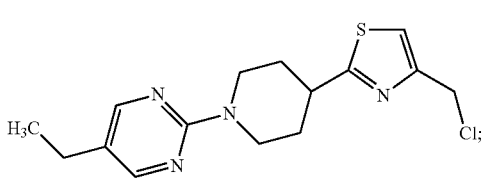
(XXIV)

(d) contacting the compound of Formula (XXIV) with a compound of Formula (VII)

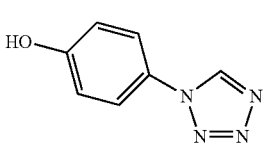
(VII)

to form 5-ethyl-2-{4-[4-(4-tetrazol-1-yl-phenoxymethyl)-thiazol-2-yl]-piperidin-1-yl}-pyrimidine.

In one embodiment, provided is a method for preparing 5-ethyl-2-{4-[4-(4-tetrazol-1-yl-phenoxymethyl)-thiazol-2-yl]-piperidin-1-yl}-pyrimidine

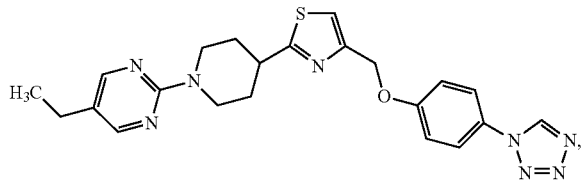 [SMILES: CCc1cnc(N2CCC(c3nc(COc4ccc(-n5cnnn5)cc4)cs3)CC2)nc1]

the method comprising:

(a) contacting a compound of Formula (IV) with acid to form a compound of Formula (XI)

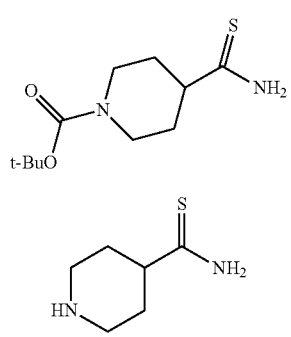

(b) contacting a compound of Formula (XXI) wherein T is a leaving group such as F, Cl, Br, I, OS(O)$_2$CF$_3$, OS(O)$_2$CH$_3$ and OS(O)CF$_3$, to form a compound of Formula (XXIII)

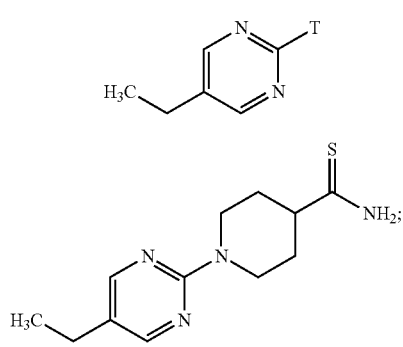

(c) contacting the compound of Formula (XXIII) with a compound of Formula (V) to form a compound of Formula (XXIV)

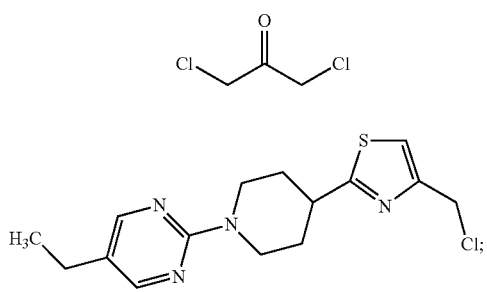

(d) contacting the compound of Formula (XXIV) with a compound of Formula (VII)

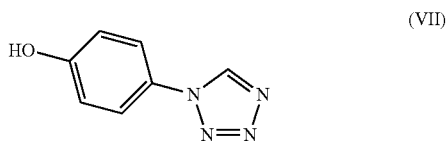 [SMILES: Oc1ccc(-n2cnnn2)cc1]

to form 5-ethyl-2-{4-[4-(4-tetrazol-1-yl-phenoxymethyl)-thiazol-2-yl]-piperidin-1-yl}-pyrimidine.

In some aspects, the compound of Formula (IX) and (X) are contacted at a temperature of 60° C. to 100° C. In other aspects, the temperature is 70° C. to 90° C., 79° C. to 81° C., or 80° C.

In some aspects, the base is NaOH, Na$_2$CO$_3$, NaHCO$_3$, KHCO$_3$, K$_2$CO$_3$, Cs$_2$CO$_3$, Et$_3$N (triethylamine) and i-Pr$_2$Net (diisopropylethylamine).

In some embodiments, the compound of Formula (IX) is prepared by contacting a compound of Formula (VIII) with acid

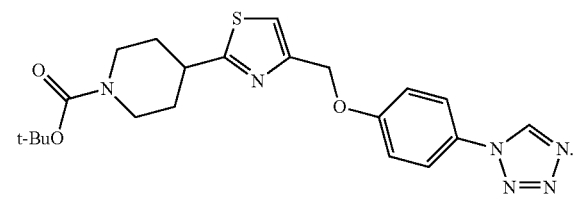

In some embodiments, the compound of Formula (VIII) is prepared by contacting a compound of Formula (VI) with a compound of Formula (VII)

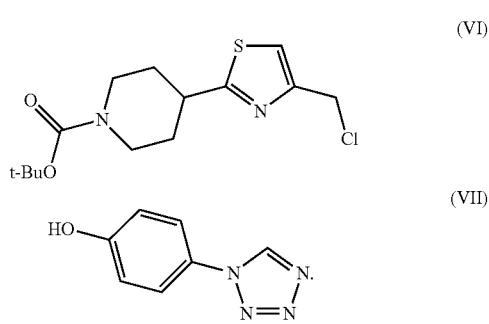

In some aspects, the compound of the compounds of Formula (VI) and Formula (VII) are contacted in a polar organic solvent selected from dimethyl formamide (DMF) and acetonitrile (MeCN) and in presence of base. In some aspects, the base is selected from the group consisting of NaOH, Na$_2$CO$_3$, K$_2$CO$_3$, Cs$_2$CO$_3$ and NaH.

In some aspects, the compound of the solvent is MeCN. In other aspects, the solvent is DMF.

In some aspects, the base is Cs$_2$CO$_3$. In still other aspects the base is K$_2$CO$_3$.

In some embodiments, the compound of Formula (VI) is prepared by contacting a compound of Formula (IV) with a compound of Formula (V)

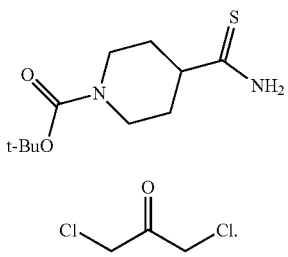 (IV)

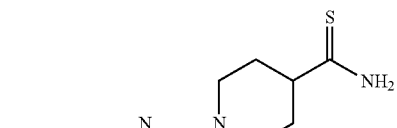 (V)

In some aspects, the compounds of Formula (IV) and Formula (V) are refluxed in a polar organic solvent in presence of base. In some such aspects, the base is selected from the group consisting of $Na_2CO_3$, $K_2CO_3$, $Cs_2CO$ and $MgCO_3$.

In some embodiments, the compound of Formula (VII) is prepared by contacting 4-aminophenol with sodium azide and trimethylorthoformate.

In some embodiments, the compound of Formula (IV) is prepared by contacting a compound of Formula (II) with a compound of Formula (III)

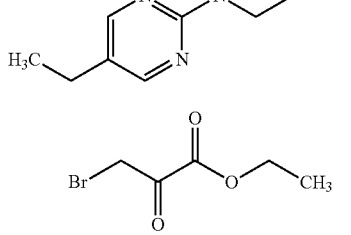 (II)

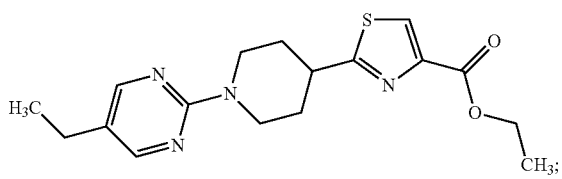 (III)

In some embodiments, the compound of Formula (II) is prepared by contacting a compound of Formula (I) with di-tert-butyl dicarbonate ($Boc_2O$).

In one embodiment provided is a method for preparing 5-ethyl-2-{4-[4-(4-tetrazol-1-yl-phenoxymethyl)-thiazol-2-yl]-piperidin-1-yl}-pyrimidine

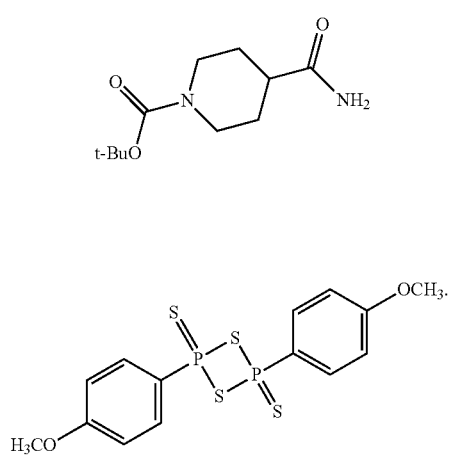

the method comprising:

(a) contacting the compound of Formula (XXIII) with a compound of Formula (XXIV) to form a compound of Formula (XXV)

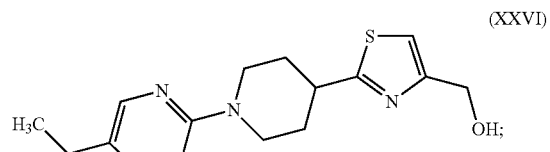 (XXIII)

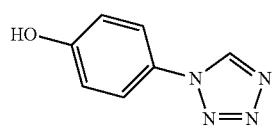 (XXIV)

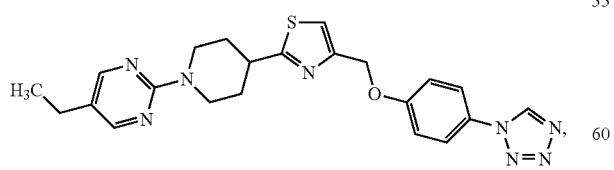 (XXV)

(b) contacting the compound of Formula (XXV) with a reducing agent, for example lithium aluminum hydride ($LiAlH_4$), lithium borohydride ($LiBH_4$), or diisobutyl aluminum hydride (DiBal) to form a compound of Formula (XXVI)

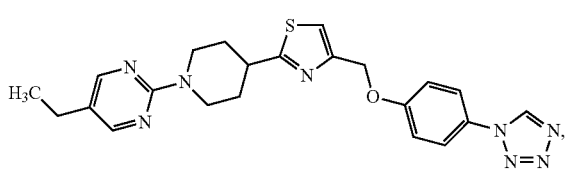 [SMILES: CCc1cnc(N2CCC(c3nc(COc4ccc(-n5cnnn5)cc4)cs3)CC2)nc1] (XXVI)

(c) contacting the compound of Formula (XXVI) with a compound of Formula (VII)

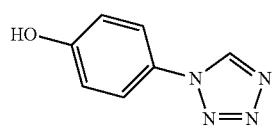

Image 7 is (VII).

under Mitsunobu coupling conditions to form 5-ethyl-2-{4-[4-(4-tetrazol-1-yl-phenoxymethyl)-thiazol-2-yl]-piperidin-1-yl}-pyrimidine.

In one embodiment provided is a method for preparing 5-ethyl-2-{4-[4-(4-tetrazol-1-yl-phenoxymethyl)-thiazol-2-yl]-piperidin-1-yl}-pyrimidine the method comprising:

(a) contacting the compound of Formula (XXIII) with a compound of Formula (XXIV) to form a compound of Formula (XXV)

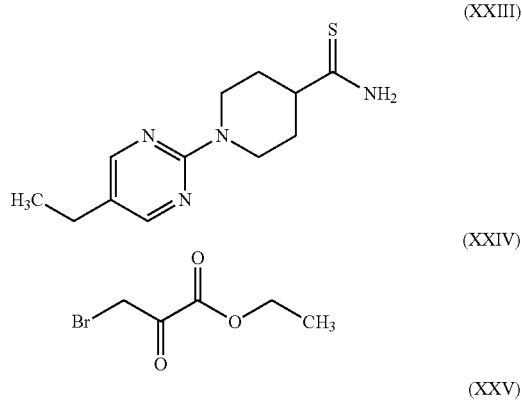

(b) contacting the compound of Formula (XXV) with a reducing agent to form a compound of Formula (XXVI)

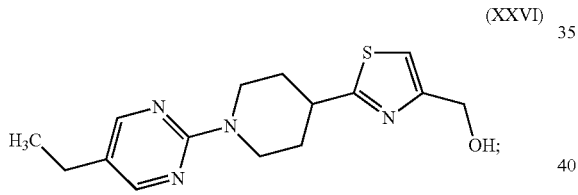

(c) converting the compound of Formula (XXVI) to a compound of Formula (XXVII) wherein Q is a leaving group such as Cl, Br, I, OS(O)$_2$CF$_3$, OS(O)$_2$CH$_3$ and OS(O)CF$_3$

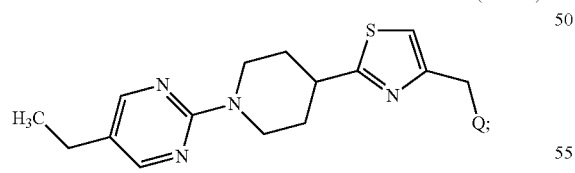

(d) contacting the compound of Formula (XXVII) with a compound of Formula (VII)

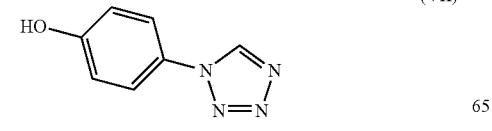

to form 5-ethyl-2-{4-[4-(4-tetrazol-1-yl-phenoxymethyl)-thiazol-2-yl]-piperidin-1-yl}-pyrimidine.

In one embodiment provided is a method for preparing 5-ethyl-2-{4-[4-(4-tetrazol-1-yl-phenoxymethyl)-thiazol-2-yl]-piperidin-1-yl}-pyrimidine

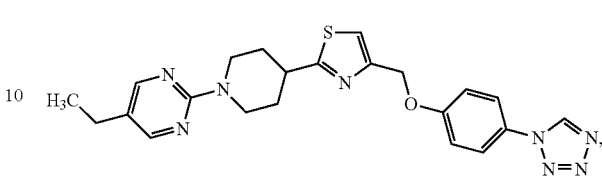

comprising contacting a compound of Formula (XXVII) wherein Q is a leaving group such as Cl, Br, I, OS(O)$_2$CF$_3$, OS(O)$_2$CH$_3$ and OS(O)CF$_3$ with a compound of Formula (VII) in presence of base, for example NaOH, Na$_2$CO$_3$, K$_2$CO$_3$, Cs$_2$CO$_3$ and NaH.

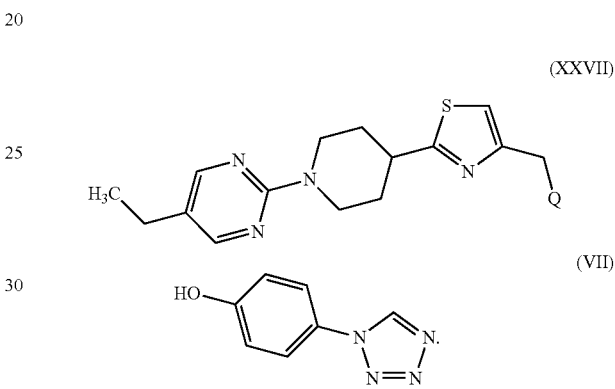

In some aspects provided is an intermediate compound for use in the preparation of 5-ethyl-2-{4-[4-(4-tetrazol-1-yl-phenoxymethyl)-thiazol-2-yl]-piperidin-1-yl}-pyrimidine selected from the group consisting of

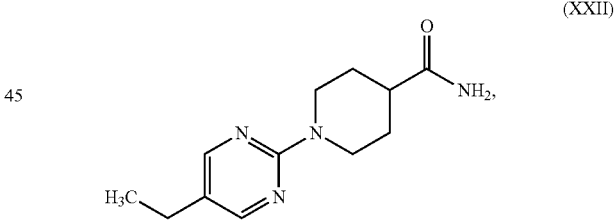

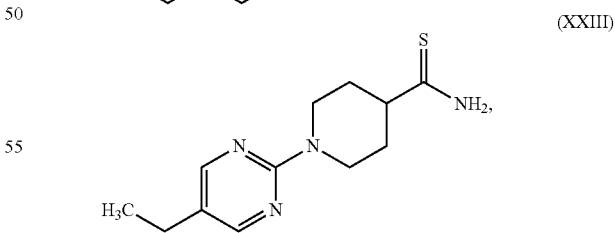

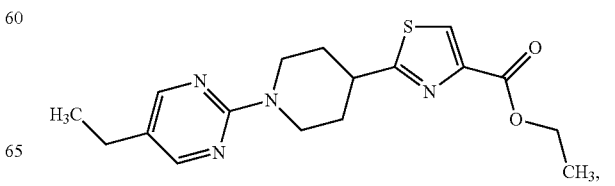

-continued

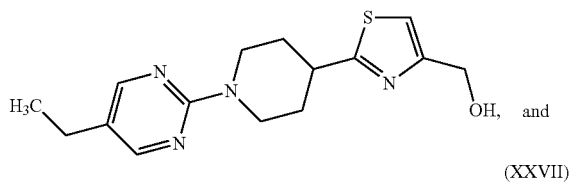

(XXVI)

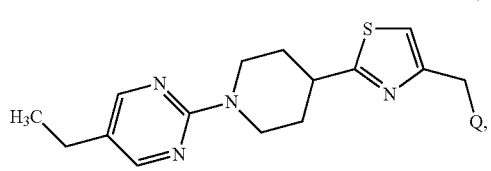

(XXVII)

wherein Q is a leaving group such as Cl, Br, I, OS(O)$_2$CF$_3$, OS(O)$_2$CH$_3$ and OS(O)CF$_3$.

In other embodiments, provided is 5-ethyl-2-{4-[4-(4-tetrazol-1-yl-phenoxymethyl)-thiazol-2-yl]-piperidin-1-yl}-pyrimidine having carbon 14 isotope labeling about the carbon atoms in the phenyl ring. The labeled compound can be prepared according to the following scheme from commercially available 14C(U)]-4-aminophenol hydrochloride (Archemi 1-800-331-6661, ARC-545):

Scheme 1

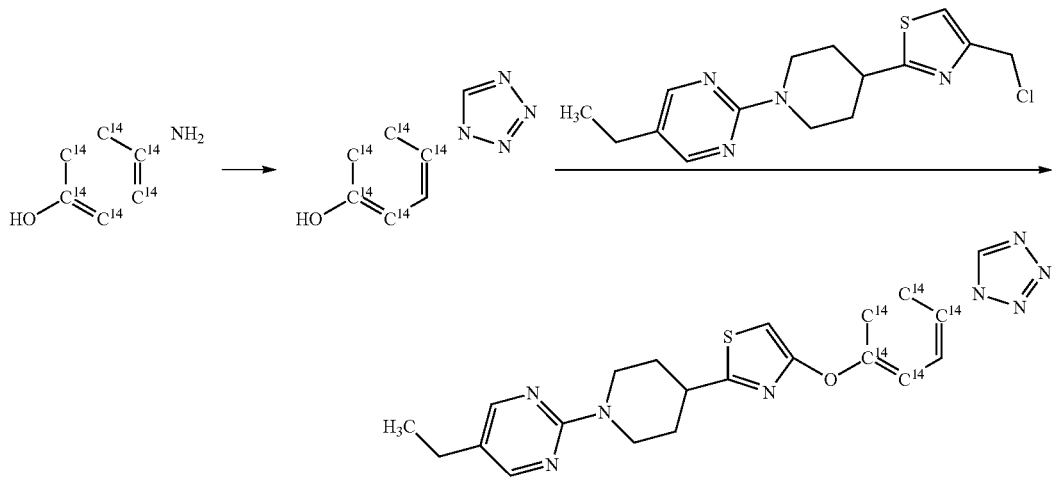

Compositions and Methods of Treatment

In accordance with the present invention methods of treating a disease or condition selected from the group consisting of Type I diabetes, Type II diabetes and metabolic syndrome are provided. The method comprises administering to a subject in need of such treatment an effective amount of a pharmaceutical formulation of the present invention.

In another aspect, methods of raising intracellular levels of Ca$^{2+}$ in a cell expressing GPR119 are provided. The method comprises exposing a cell that expresses GPR119 to a pharmaceutical formulation of the invention. Ca$^{2+}$ levels can be determined by methods known in the art.

In one embodiment, the cell that expresses GPR119 is a pancreatic cell, an islet cell, or a beta cell, an intestinal endocrine cell, an L cell or a K cell.

Another aspect of the invention provides a method of stimulating insulin production in a mammal, in particular a human. The method comprises administering an effective amount of a pharmaceutical formulation of the invention to the mammal. In response to administration of a compound to the subject, insulin is produced by the beta cells. Methods by which a skilled artisan can measure insulin secretion in laboratory animals in response to administration of a pharmaceutical formulation of the invention are known in the art.

In another aspect, the invention provides a method of stimulating insulin secretion in a mammal, in particular a human. The method comprises administering an effective amount of a pharmaceutical formulation of the invention to the mammal. In response to administration of a pharmaceutical formulation to the subject, insulin is secreted into the blood stream by the beta cells.

A further aspect of the invention provides a method of stimulating glucose-dependent insulin secretion in a mammal, in particular a human. The method comprises administering an effective amount of a pharmaceutical formulation of the invention to the mammal. After administration to the subject, insulin is secreted into the blood stream by the beta cells in a glucose-dependent manner. Methods that show the blood glucose lowering effects of the pharmaceutical formulations of the invention are known in the art.

In another embodiment, the invention provides methods of lowering blood glucose in a mammal, preferably a human. The method comprises administering an effective amount of a pharmaceutical formulation of the invention to the mammal. In response to administration of a pharmaceutical formulation to the subject, blood glucose levels are lowered. In one embodiment, the blood glucose in a mammal is reduced by about 5% or more, or about 15% or more, or about 25% or more, or about 35% or more, or about 45% or more, or about 50% or more, or about 60% or more, or about 70% or more, or about 75% or more, or about 80% or more, or about 85% or more, or about 90% or more.

In some embodiments, the method further comprises steps to measure blood glucose levels before and after administration of a pharmaceutical formulation of the invention. Blood glucose levels are easily measured by numerous commercially available glucose monitoring devices that measure blood glucose from samples of blood or urine. Blood glucose can also be measured by commercially available glucometers that do not require blood or urine samples.

Methods that teach how to measure improvements in diabetes parameters, including blood glucose monitoring are known in the art.

Another aspect of the invention provides a method of stimulating incretin production in a mammal, in particular a human. The method comprises administering an effective amount of a pharmaceutical formulation of the invention to the mammal. In response to administration of a pharmaceutical formulation to the subject, glucagon-like peptide 1 and glucose-dependent insulinotropic polypeptide is produced by the intestinal endocrine cells. Methods by which a skilled artisan can measure incretin production in laboratory animals in response to administration of a pharmaceutical formulation of the invention are known in the art.

The present invention will be described in further detail by the following examples. It is to be understood, however, that these examples are given for illustrative purpose only and are not construed to limit the scope of the present invention.

EXAMPLES

The present invention will be described in further detail by the following examples. It is to be understood, however, that these examples are given for illustrative purpose only and are not construed to limit the scope of the present invention.

Example 1

4-Carbamoyl-piperidine-1-carboxylic acid tert-butyl ester

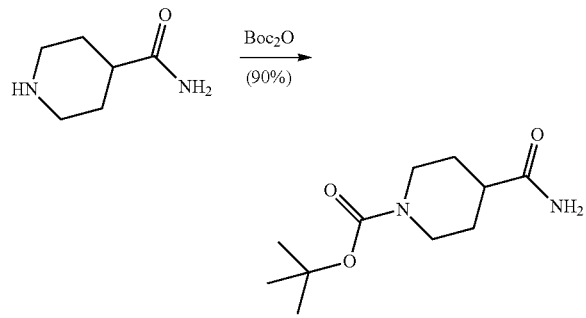

To a suspension of iosnipecotamide (255 g, 1.99 mol) and 4-dimethylamino-pyridine (204 mg, 1.82 mol) in methylene chloride (1500 mL) in a 5-lite of three-neck flask was added a solution of di-tert-butyl dicarbonate (502 g, 2.30 mol, 1.15 eq.) in methylene chloride (500 mL) dropwise at room temperature with mechanic stirring. A clear solution was reached at the end of the adding. After stirring at room temperature for two more hours, the solution was washed with phosphoric acid water solution (2.5 v/v %, 500 mL), water (500 mL), half saturated sodium bicarbonate water solution (500 mL), and 10% of brine (500 mL). The organic phase was dried over anhydrous sodium sulfate. During the course of removing of the methylene chloride, ethyl acetate (100 ml) and heptane (200 mL) was added. After removing the methylene chloride, the white solid formed was filtrated, washed with hexane, and dried to give 414 g (95%) of product.

TLC: dichloromethane-methanol 90:10, Rf (product)=0.28; Rf (starting material)=base line, iodine positive.

Example 2

4-Thiocarbamoyl-piperidine-1-carboxylic acid tert-butyl ester

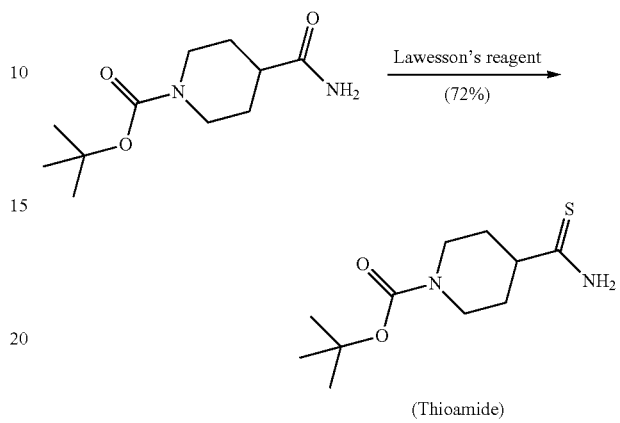

(Thioamide)

To a suspension of 4-Carbamoyl-piperidine-1-carboxylic acid tert-butyl ester (288 g, 1.26 mol) in dimethoxyethane (2000 mL) and methylene chloride (800 mL) in a 5-lite of three-neck flask was added Lawesson's Reagent (255 g, 0.63 mol). The mixture was stirred at room temperature for 80 min. TLC check there was no starting material left. The solvents were removed under vacuum. The residue was dissolved in ethyl acetate (1500 mL), and washed with half saturated potassium carbonate water solution (500 mL each, two times), 50% of brine (500 mL). The organic phase was dried over anhydrous sodium sulfate and concentrated to dry. The obtained solid was dissolved in ethyl acetate (1000 mL) and filtered at hot to remove insoluble white stuff. To the solution was added heptane (300 mL). After removing most of ethyl acetate, the solid formed was filtrated, washed with hexane-ether (1:1), and dried to give 252 g (82%) of product.

TLC: dichloromethane-methanol 90:10, Rf (product)=0.37, UV and iodine positive; Rf (starting material)=0.28, iodine positive.

Example 3a

4-Tetrazo-1-ly-phenol

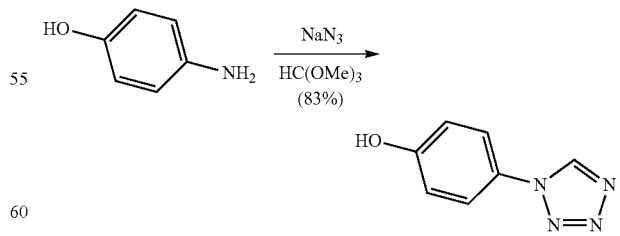

To a 2-liter one-neck flask under air, immersed in an oil bath and fitted with a refluxing condenser, was added 4-aminophenol (50 g, 0.459 mol), acetic acid (500 mL), sodium azide (41.7 g, 0.642 mol), and trimethyl orthoformate (70 mL, 68 g, 0.642 mol). The mixture was stirred at 60° C. (oil bath) for one hour and then refluxed (oil bath, 100° C.) for 3 hours. A clear solution was formed during the refluxing. The temperature of solution was lowered to 80° C. (oil bath) and water (300 mL) was added slowly. The temperature of the solution was cooled down to room temperature. The solid formed over night was filtered and dried to give 61.7 g (83%) of product as first crop.

TLC: hexane-ethyl acetate 50:50, Rf (product)=0.28; Rf (starting material)=0.23, UV and iodine positive.

$^1$HNMR (400 MHz, $D_3$COD), δ 9.58 (s, 1H), 7.61 (d, J=9.0 Hz, 2H), 6.97 (d, J=9.0 Hz, 2H) ppm.

Modified procedure: The reactions were carried out at 1.5 times of the abovementioned scale. A 2-liter flask under air was charged with acidic acid followed by 4-aminophenol, sodium azide, and trimethyl orthoformate with stirring at room temperature. The flask was fitted with a bump trap and was heated to 100° C. (oil bath) during the course of 1 to 1.5 hours. Solid started to precipitate and the temperature of mixture was lowered to 80° C. Water was added and the mixture was cooled down to room temperature. The mixture was filtered and the solid was washed with water and dried to give the desired product (>88% yield).

$^1$HNM (400 MHz, $D_3$COD), δ 9.58 (s, 1H), 7.61 (d, J=9.0 Hz, 2H), 6.97 (d, J=9.0 Hz, 2H) ppm.

Example 3b

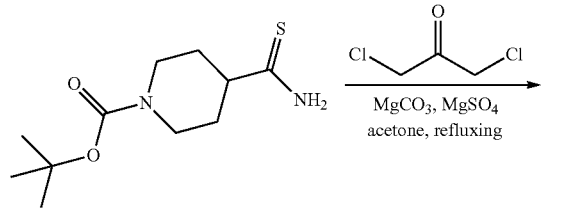

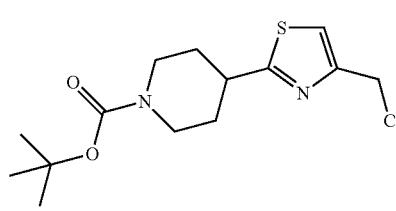

To a 500 mL flask under air, immersed in an oil bath and a condenser, was added 4-thiocarbamoyl-piperidine-1-carboxylic acid tert-butyl ester (29 g, 120 mmol), acetone (300 mL) $MgSO_4$ (21.6 g, 180 mmol) and $MgCO_3$ (10 g, 120 mmol), 1,3-dichloroacetone (19.8 g, 156 mmol). The resulting mixture was heated under reflux overnight, cooled and filtered through celite. The solvent was removed in vacuo and the residue was redissolved with EtOAc (500 mL). The resulting solution was washed successively with 5% $NaHSO_3$ (twice), saturated $NaHCO_3$ and brine. After drying ($NaSO_4$), the solvent was removed to afford 35 g of the title compound as light yellow oil. The oil became dark solid after standing at room temperature. The color could be removed by activated charcoal. The purity was improved from 92% to 96%. $^1$H NMR ($CDCl_3$): δ 7.20 (1H, s), 4.67 (2H, s), 4.20 (2H, br), 3.16 (1H, m), 2.87 (2H, m), 2.09 (2H, m), 1.72 (2H, m), 1.47 (9H, s).

Example 4

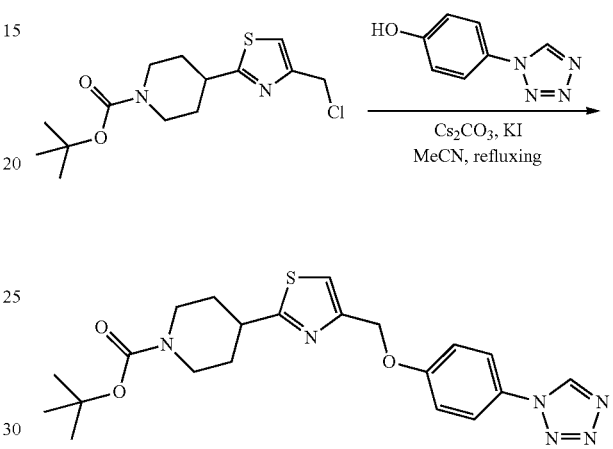

A mixture of 4-(4-chloromethyl-thiazol-2-yl)-piperidine-1-carboxylic acid tert-butyl ester (35 g, 0.11 mol), 4-tetrazol-1-yl-phenol (21.4 g, 0.132 mol), $Cs_2CO_3$ (43 g, 0.132 mol), KI (1.8 g, 11 mmol) in acetonitrile (400 mL) was heated under reflux overnight. After cooling, the solid was filtered through a pad of celite. The filtrate was concentrated in vacuo. The residue was dissolved in methylene chloride and washed with 5% aqueous NaOH (3 times), water and brine. After drying ($NaSO_4$), the solvent was removed. The resulting solid was dissolved in ethyl acetate. The resulting solution was heated with activated charcoal and filtrated through a pad of celite. The filtrate was concentrated and the residue was purified by recrystallization from EtOAc/Hexane to afford 37 g desired product.

$^1$H NMR ($CDCl_3$): δ 8.01 (1H, s), 7.61 (2H, d, J=8.8 Hz), 7.25 (1H, s), 7.15 (2H, d, J=8.8 Hz), 5.22 (2H, s), 4.2 (2H, br), 3.17 (1H, m), 2.87 (2H, m), 2.11 (2H, m), 1.73 (2H, m), 1.46 (9H, s).

Example 5

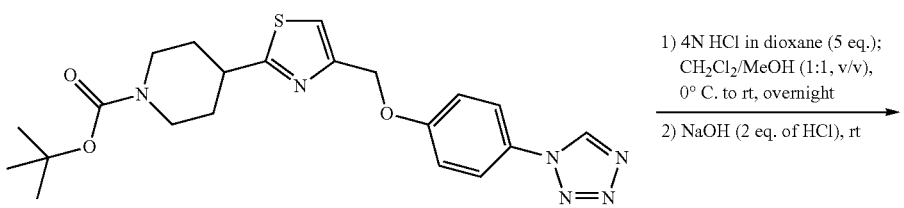

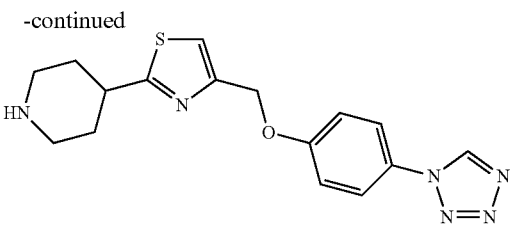

To a 3-L 3-neck flask under N₂ fitted with an addition funnel, was added 400 mL of anhydrous methylene chloride (J. T. Baker low water grade; the CH₂Cl₂ will facilitate the solubility of substrate) and 115.59 g of t-butyl carbamate substrate (0.26 mol) in one-portion. After stirring at rt for 2~5 minutes, to the resulting almost clear solution was added 400 mL of methanol (J. T. Baker HPLC grade). The resulting clear brown solution was cooled to 0-4° C. (ice-water bath temperature) with stirring, and then 330 mL of 4N HCl in 1,4-dioxane (1.32 mol, 5 eq.) was added dropwise over 30 minutes. The ice-water bath was removed, and the resulting brown homogeneous solution was stirred at rt overnight (15 hours). At least 7 hours is needed to bring the reaction to completion. The reaction mixture was aliquoted and quenched into 2N NaOH, and then extracted w/ EtOAc. ¹H NMR in DMSO-d₆. Diagnostic peaks: free-amine product δ 7.63 (s, 1H); starting material (substrate) δ 7.66 (s, 1H). Typically, the conversion was estimated via the integral of the italicized signals: 4 hrs, 80% conversion; 6 hrs, 95% conversion. The reaction solution was allowed to cool to 10° C. (ice-water bath temp), and then a solution of 15% (w/v) NaOH (705 mL; 2.64 mol, 2 eq. of HCl used) in ~500 mL of water was added dropwise over 15 minutes. (Diluted 15% aq. NaOH was used to ensure no precipitation (inorganic salt) in the organic phase). Immediate phase break was observed when the stirring was stopped to give a brown aqueous layer on top and a pale yellow organic layer on the bottom. The organic layer was collected, and the remaining aqueous layer was extracted with CH₂Cl₂ (500 mL×2). The organic layers were combined, rinsed with ~500 mL of water, and dried over anhy. Na₂SO₄. After most of solvents were removed in vacuo, precipitation began. To this pale yellow mixture was added 500 mL of heptane to give a pale yellow slurry. The resulting precipitate was collected on a filter funnel, and the mother liquor was stripped down. The combined solids were rinsed with heptane (200 mL). After air-drying overnight, 84.1 g (94% yield) of free amine was obtained as a white or an off-white solid.

¹H NMR (DMSO-d₆): δ 9.98 (1H, s), 7.80 (2H, d, J=8.0 Hz), 7.63 (1H, s), 7.28 (2H, d, J=8.0 Hz), 5.20 (2H, s), 3.05 (1H, m), 2.97 (2H, m), 2.56 (2H, m), 1.93 (2H, m), 1.55 (2H, m) ppm.

Instead of using HCl, if the reaction was treated with 5 eq. TFA in CH₂Cl₂ at rt, ~50% of an unknown by-product will be generated which can be seen by taking a ¹H NMR in DMSO-d₆: Diagnostic peaks δ 7.45 (1H, s), 6.61 (2H, d, J=8.8 Hz), 6.44 (2H, d, J=8.8 Hz), 4.89 (2H, s) ppm. The use of CH₂Cl₂/CH₃OH as co-solvents will eliminate the formation of impurities seen with other solvents. The use of 1,4-dioxane, 1,4-dioxane/methanol, or methylene chloride will produce a tiny amount of detectable impurity which can be seen by ¹H NMR in DMSO-d₆: Diagnostic peaks δ 6.82 (m), 6.56 (m), 4.99 (m) ppm. This impurity will be carried over to the final product in the next step, and cannot be removed by purification via recrystallization.

Example 6

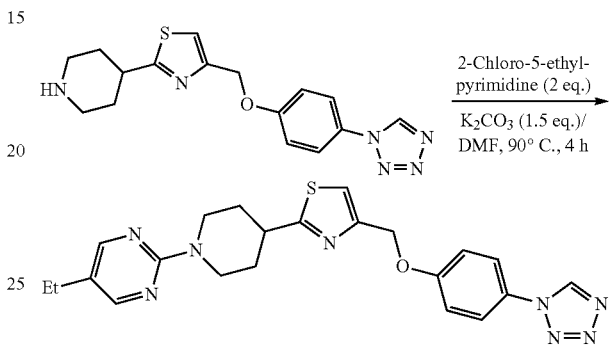

To a 3-L 3-neck flask under N₂ was added 105.7 g of crude free amine (0.31 mol), 88.0 g of 2-chloro-5-ethylpyrimidine (0.62 mol, 2 eq.) in one-portion, and then 800 mL of anhydrous DMF. After stirring at rt for 1~2 minutes, to the resulting clear solution was added 64.0 g of anhy. K₂CO₃ (0.46 mol, 1.5 eq.) in one-portion. The flask was immersed in a pre-heated oil bath (90° C., oil-bath temperature), and the reaction mixture was stirred at 90° C. (oil-bath temperature) for 3.5 hours. The reaction mixture was aliquoted and quenched into water/brine, and then extracted w/ EtOAc. ¹H NMR in DMSO-d₆. Diagnostic peaks: product δ 7.66 (s, 1H); free-amine (starting material) δ 7.63 (s, 1H); pyrimidine δ 8.67 (s, 2H), DMF δ 7.03 (s, 1H). Typically, the conversion was estimated via the integral of the italicized signals. Complete conversion was observed between 3 to 4 hours. Prolonged heating (>5 hours) resulted in the formation of the unidentified impurity.

The reaction mixture was transferred to a 5-L 3-neck flask, and allowed to cool with stirring to rt with ice-water bath. To the reaction mixture at rt under stirring vigorously (mechanical stirrer) and approximate 2000 mL of water was added slowly dropwise over 30 minutes to give an off-white slurry (precipitation began when ~500 mL of water was added). After the addition was finished, the resulting slurry was stirred at rt for an additional 10~15 minutes. The off-white precipitate was filtered and then rinsed with water (250 mL×2). After air-drying overnight, approximate 387 g of wet off-white solid was obtained, and redissolved in 1500 mL of EtOAc by heating at 55° C. (internal solution temperature) for ca. 10 minutes. The resulting pale-yellow solution was washed with water (250 mL×3) and water/brine (200 mL/100 mL), and dried over anhy. Na₂SO₄. After most of solvents were removed in vacuo, precipitation began and then gave an off-white slurry (~500 mL of solvents left). The resulting white precipitate was collected on a filter funnel, and rinsed with EtOAc (300 mL×2). The mother liquor was kept to do another recrystallization later on, and the precipitate on the filter funnel was rinsed once more time with 300 mL of heptane. After air-drying, 91.11 g of product was obtained as a white solid. The mother liquor (without heptane) was stripped down in vacuo until a thick slurry was formed, and the resulting precipitate was filtered and rinsed twice with EtOAc (100 mL×2) and once with heptane (100 mL) to give another 16.84 of product as a white solid. Overall yield 78%.

$^1$H NMR (DMSO-d$_6$): δ 9.98 (1H, s), 8.24 (2H, s), 7.80 (2H, d, J=6.8 Hz), 7.66 (1H, s), 7.28 (2H, d, J=6.8 Hz), 5.20 (2H, s), 4.67 (2H, m), 3.32 (1H, m), 3.01 (2H, m), 2.43 (2H, q, J=7.2 Hz), 2.07 (2H, m), 1.59 (2H, m), 1.11 (3H, t, J=7.2 Hz) ppm. All the remaining mother liquors were combined, and concentrated in vacuo to give 15.07 g of an off-white solid which would be purified by one more time recrystallization with EtOAc or chromatography with 70% EtOAc/hexanes on silica gel.

This reaction was also tried at a small scale (0.6 mmol) at higher concentrations (0.6 M with 2 eq. of pyrimidine and 1.2 M with 1.3 eq. of pyrimidine).

Free amine (207 mg, 0.60 mmol) was treated at 90° C. with 178.3 mg of 2-chloro-5-ethylpyrimidine (2 eq.) and anhy. K$_2$CO$_3$ (1.5 eq.) in 1 mL of DMF (the final concentration of the free amine is ~0.60 M). The reaction was complete in 2 hours. However, the reaction mixture was not homogenous at the end because of the precipitation of product.

Free amine (212 mg, 0.62 mmol) was treated at 90° C. with 114.2 mg of 2-chloro-5-ethylpyrimidine (1.3 eq.) and anhy. K$_2$CO$_3$ (1.5 eq.) in 0.5 mL of DMF (the final concentration of the free amine is ~1.2 M). The reaction was achieved ~85% conversion in 2 hours, and the reaction mixture was not homogenous because of the precipitation of product. Significant amount of the unidentified by-products were formed after heating at 90° C. for 4 hours.

Example 7

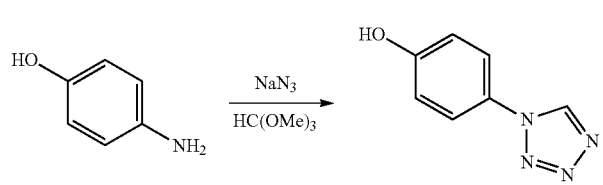

4-Tetrazol-1-yl-phenol

To a Kimax tube (25×150 mm) were added 4-aminophenol (200 mg, 1.83 mmol), sodium azide (167 mg, 2.57 mg, 1.4 eq.), acetic acid (1 mL), 2 drops of concentrated hydrochloride acid, and trimethyl orthoformate (0.5 mL) at room temperature. The mixture was stirred, and heated up to 100° C. on a heating block. After at 100° C. for 20 min, the temperature was lowered to 80° C., and water (1 mL) was added. When the mixture was cooled down to room temperature, the liquids were removed using pipette. The solid was washed with water (1 mL×3) and heptane (1 mL), and tried under vacuum. The white solid was used in the next step without further purification.

TLC: hexane-ethyl acetate 50:50, Rf (product)=0.28; Rf (starting material)=0.23, UV and iodine positive.

$^1$HNMR (400 MHz, D$_3$COD), δ 9.58 (s, 1H), 7.61 (d, J=9.0 Hz, 2H), 6.97 (d, J=9.0 Hz, 2H) ppm.

To the same tube from above reaction (with the synthesized 4-tetrazol-1-yl-phenol in) were added 2-[4-(4-Chloromethyl-thiazol-2-yl)-piperidin-1-yl]-5-ethyl-pyrimidine (571-110, 532 mg, 1.65 mmol), Cs$_2$CO$_3$ (596 mg, 1.83 mmol), KI (14 mg) in acetonitrile (2 mL). The mixture was heated at 60° C. for 10 hours (The reaction was followed by HPLC/MS).

After cooling the reaction mixture was treated with ethyl acetate (100 mL) and water (20 mL). The water phase was separated out. The organic phase was washed with brine (20 mL), dried over anhydrous sodium sulfate, concentrated. The residue was dissolved in small amount of dichloromethane and purified by 40 g silica gel Combiflash column to afford 580 mg (70% yield in two steps) of desired product as white solid.

$^1$H NMR (DMSO-d$_6$): δ 9.98 (1H, s), 8.24 (2H, s), 7.80 (2H, d, J=6.8 Hz), 7.66 (1H, s), 7.28 (2H, d, J=6.8 Hz), 5.20 (2H, s), 4.67 (2H, m), 3.32 (1H, m), 3.01 (2H, m), 2.43 (2H, q, J=7.2 Hz), 2.07 (2H, m), 1.59 (2H, m), 1.11 (3H, t, J=7.2 Hz) ppm. MS (ESI), m/z 449.

Example 8

Melt Extrusion Formulations

Solid dispersion formulations were prepared using the Leistritz 16-mm extruder, examining the effect of polymer type, drug loading and processing temperature on the critical product attributes of Compound A solid dispersions. Exemplifying process conditions and formulation variables are presented in Table 1.

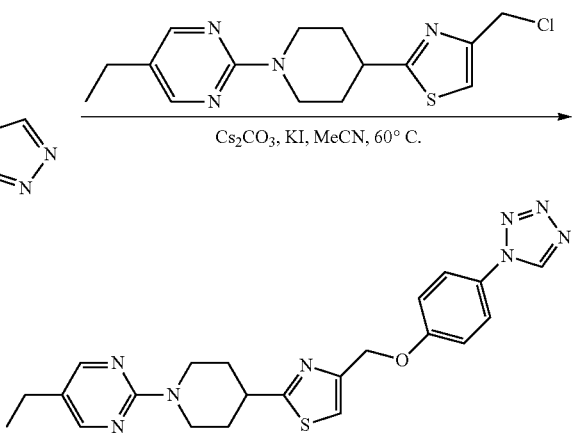

TABLE 1

Processing Parameters Used For Production of Compound A Solid Dispersion Formulations by Melt Extrusion on the 16-mm Extruder

| Formulation | Loading (mg/g) | Polymer | Barrel Temperature (° C.) | Screw Speed (rpm) |
|---|---|---|---|---|
| 1 | 250 | HPMCAS-MF | 125 | 250 |
| 2 | 250 | Eudragit® E PO | 125 | 250 |

TABLE 1-continued

Processing Parameters Used For Production of Compound A Solid Dispersion Formulations by Melt Extrusion on the 16-mm Extruder

| Formulation | Loading (mg/g) | Polymer | Barrel Temperature (° C.) | Screw Speed (rpm) |
|---|---|---|---|---|
| 3 | 250 | Kollidon ® VA 64 | 125 | 250 |
| 4 | 250 | Eudragit ® L100-55 | 160 | 100-250 |
| 5 | 400 | Kollidon ® VA 64 | 130 | 250 |
| 6 | 400 | Eudragit ® E PO | 130 | 250 |

Figure 2:
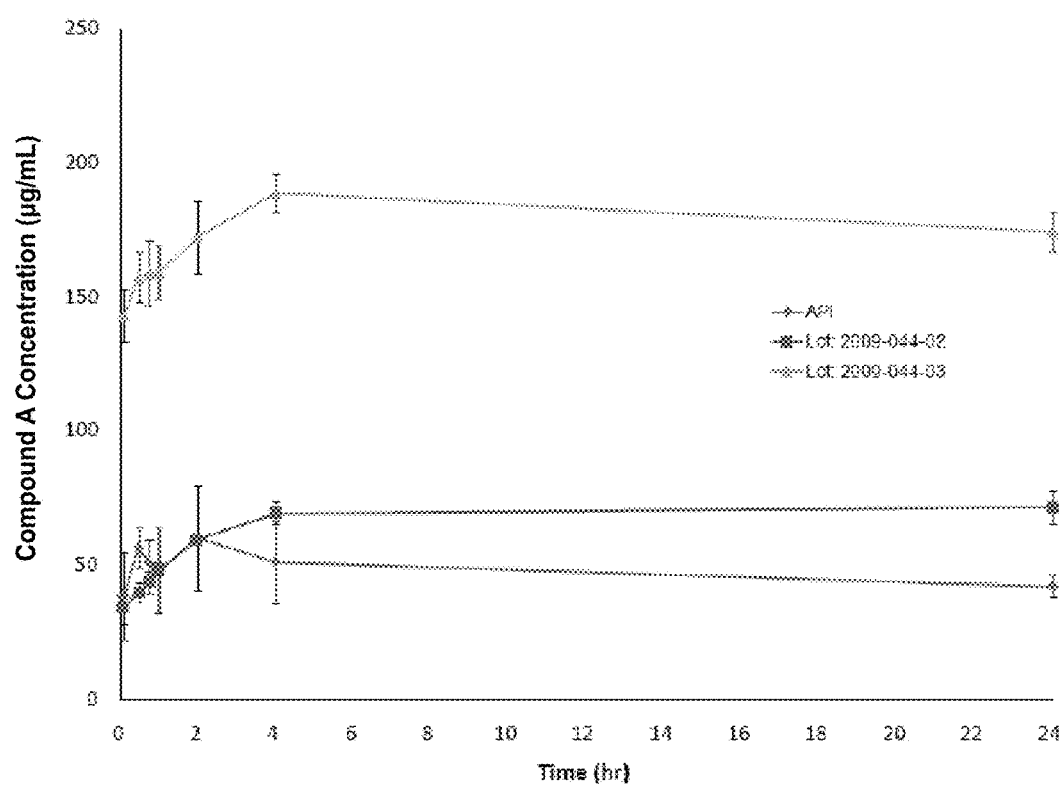
FIG. 2 provides a non-sink dissolution profile for Compound A melt extruded compositions tested in simulated fed state intestinal fluid.
Figure 3:
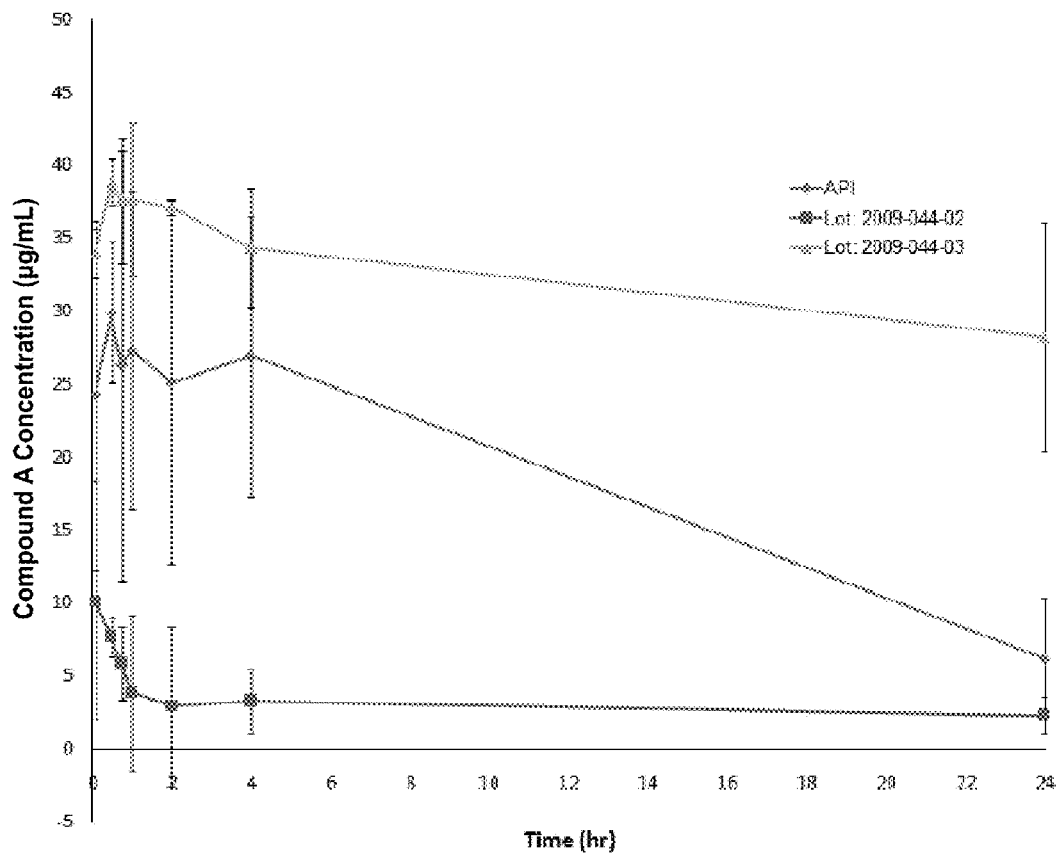
FIG. 3 provides a non-sink dissolution profile for Compound A melt extruded compositions tested in simulated fasted state intestinal fluid.

HPMCAS-MF indicates M grade Hypromellose Acetate Succioate supplied as a fine power Solid dispersion formulations of Compound A in Eudragit® E PO (Formulation 2) and Kollidon® VA 64 (Formulation 3) were examined for dissolution behavior under non-sink conditions to assess oral bioavailability enhancement. Studies were conducted in three different media preparations, including: simulated gastric fluid, fed state simulated intestinal fluid and fasted state simulated intestinal fluid, which are presented in Table 2, Table 3 and Table 4 and FIG. 1, FIG. 2 and FIG. 3.

TABLE 2

Non-Sink Dissolution Performance of Compound A Melt Extruded Formulations Tested in Simulated Gastric Fluid

| Formulation | Compound A Crystalline | Compound A Extrudate in Eudragit ® VA 64, 250 mg/g | Compound A Extrudate in Kollidont ® VA 64, 250 mg/g |
|---|---|---|---|
| $C_{max}$ (mg/mL) | 0.247 | 1.547 | 1.307 |
| $T_{max}$ (hr) | 2 | 0.08 | 0.5 |
| $AUC_{0-2\ hr}$ (mg * hr/mL) | 0.321 | 2.484 | 2.454 |
| $AUC_{0-4\ hr}$ (mg * hr/mL) | 0.727 | 4.931 | 5.021 |
| $AUC_{0-24\ hr}$ (mg * hr/mL) | 4.494 | 27.324 | 29.714 |

TABLE 3

Non-Sink Dissolution Performance of Compound A Melt Extruded Compositions Tested in Simulated Fed State Intestinal Fluid

| Formulation | Compound A Crystalline | Compound A Extrudate in Eudragit ® VA 64, 250 mg/g | Compound A Extrudate in Kollidont ® VA 64, 250 mg/g |
|---|---|---|---|
| $C_{max}$ (μg/mL) | 60.182 | 71.649 | 188.372 |
| $T_{max}$ (hr) | 2 | 24 | 4 |
| $AUC_{0-2\ hr}$ (μg * hr/mL) | 100.045 | 91.584 | 307.367 |
| $AUC_{0-4\ hr}$ (μg * hr/mL) | 211.597 | 220.744 | 667.833 |
| $AUC_{0-24\ hr}$ (μg * hr/mL) | 1148.003 | 1631.674 | 4294.733 |

TABLE 4

Non-Sink Dissolution Performance of Compound A Melt Extruded Compositions Tested in Simulated Fasted State Intestinal Fluid

| Formulation | Compound A Crystalline | Compound A Extrudate in Eudragit ® VA 64, 250 mg/g | Compound A Extrudate in Kollidon ® VA 64, 250 mg/g |
|---|---|---|---|
| $C_{max}$ (μg/mL) | 29.891 | 10.122 | 38.858 |
| $T_{max}$ (hr) | 0.50 | 0.08 | 0.50 |
| $AUC_{0-2\ hr}$ (μg * hr/mL) | 51.205 | 9.964 | 71.508 |
| $AUC_{0-4\ hr}$ (μg * hr/mL) | 103.281 | 16.145 | 143.005 |
| $AUC_{0-24\ hr}$ (μg * hr/mL) | 434.380 | 71.762 | 768.998 |

Example 9

Spray-Dried Dispersion Formulation with 25% of Compound A

Figure 4:
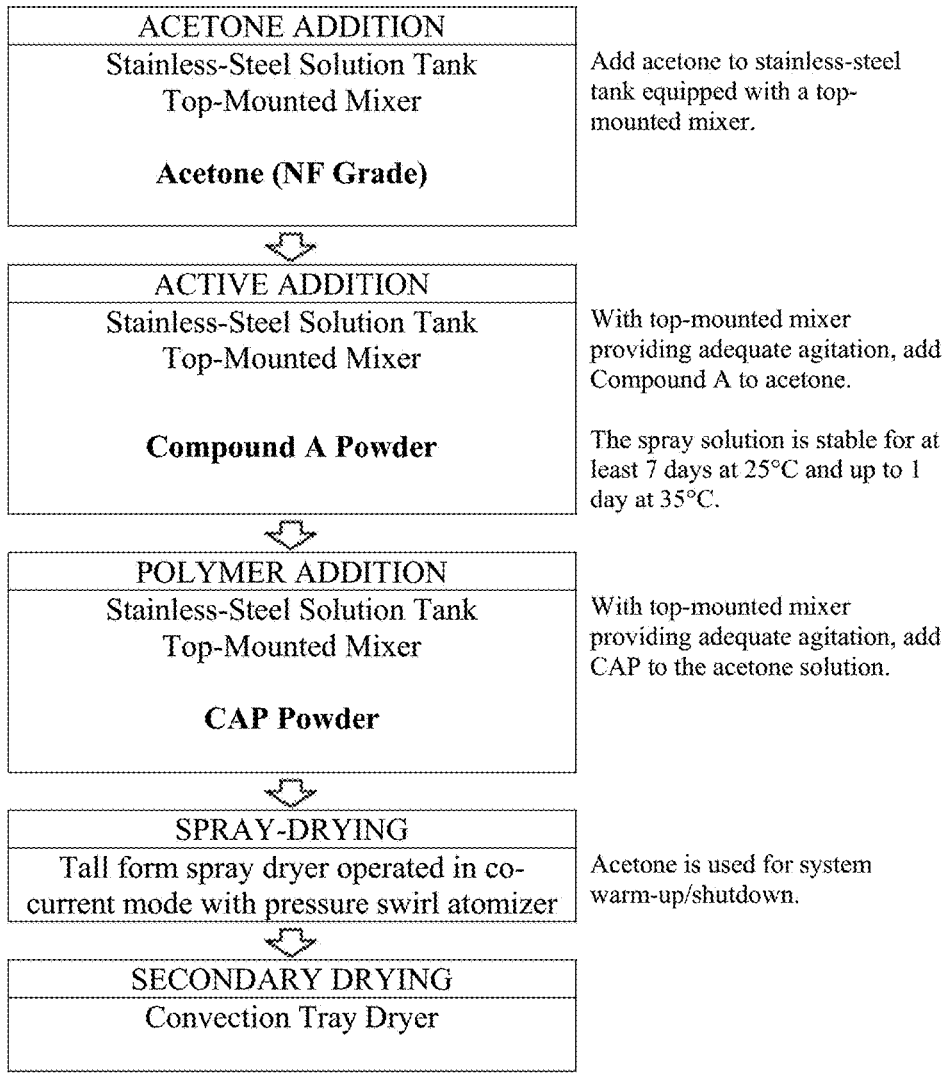
FIG. 4 provides a flow chart for a manufacture process of the 25% Compound A:CAP spray-dried dispersion (SDD).

The spray drying process includes preparation of the spray solution to dissolve Compound A and cellulose acetate phthalate (CAP), spray drying to form spray-dried dispersion (SDD) powder, and secondary drying of the SDD powder to remove residual solvent. FIG. 4 provides an overview of the process used to manufacture the 25% SDD formulation containing 250 mg/g of Compound A and 750 mg/g of CAP (referred to as 25% Compound A: CAP SDD) on a PSD-1 spray dryer.

Spray Solution Preparation: During spray solution preparation the temperature of the solution is maintained at room temperature but above 20° C. to ensure the solubility of Compound A. After Compound A is added to the acetone, the solution is mixed for at least one hour, until the crystalline Compound A is completely dissolved. The CAP is then added to the solution and mixed for at least one hour until the CAP is completely dissolved. The spray solution contains 1.25% of Compound A, 3.75% of CAP and 95% of acetone.

Spray Drying: The spray-drying conditions are divided into preheating, warm-up/shutdown and feed-solution processing phases. During the warm-up phase pure acetone is sprayed to thermally equilibrate the spray dryer. During the feed-solution processing phase the Compound A:CAP spray solution is sprayed.

The operating conditions for the three phases are summarized in Table 5.

TABLE 5

Spray-Drying Conditions for Manufacture of 25% A Compound A:CAP SDD

| Process | Process Parameters | Target | Target Range |
|---|---|---|---|
| (A) Preheating | Nitrogen drying-gas flow | 1850 g/min | 1550 to 2150 g/min |
| | $T_{in}$ | 125° C. | 115° C. to 135° C. |

TABLE 5-continued

Spray-Drying Conditions for
Manufacture of 25% A Compound A:CAP SDD

| Process | Process Parameters | Target | Target Range |
|---|---|---|---|
| (B) Warm-Up/ Shutdown | Nitrogen drying-gas flow | 1850 g/min | 1550 to 2150 g/min |
|  | $T_{in}$ | 125° C. | 155° C. to 135° C. |
|  | $T_{out}$ | 47° C. | 42° C. to 52° C. |
|  | Acetone atomization pressure | 295 psi | 195 to 395 psi |
|  | Acetone feed rate | 195 g/min | 160 to 200 g/min |
| (C) Feed-Solution Processing | Nitrogen drying-gas flow | 1850 g/min | 1550 to 2150 g/min |
|  | $T_{in}$ | 125° C. | 115° C. to 135° C. |
|  | $T_{out}$ | 45° C. | 40° C. to 50° C. |
|  | Solution atomization pressure | 315 psi | 215 to 415 psi |
|  | Solution feed rate | 215 g/min | 200 to 230 g/min |

Figure 5:
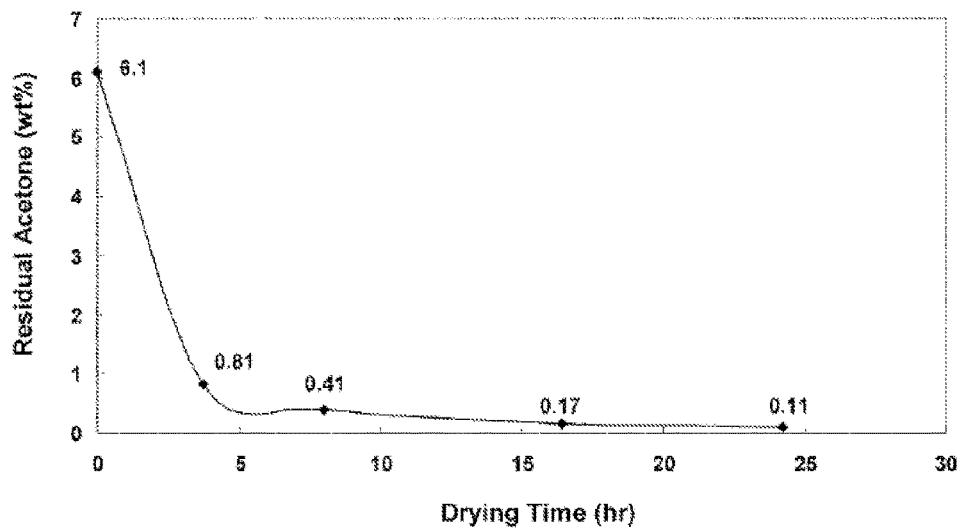
FIG. 5 illustrates the residual acetone content as a function of tray-drying time at 40° C./30% relative humidity (RH) for the 25% Compound A:CAP SDD, based on a headspace gas chromatography (GC) analysis.

In one embodiment, the spray-drying conditions are:
pressure nozzle: SK 76-16
drying-gas inlet temperature ($t_{in}$): 125° C.±10° C.
dryer outlet temperature ($t_{out}$): 45° C.±5° C.
nitrogen drying-gas flow: 1850±300 g/min
solution feed rate: 215±15 g/min
atomization pressure: 315±100 psig
product collection: 6-inch outer-diameter cyclone
solution feed filter: ≤230 μm Secondary Drying: The SDD powder is spread evenly on open trays and placed in a tray dryer and dried overnight to remove residual acetone (in-process control: residual acetone <0.2%). Drying parameters are listed below:
Tray Dryer Type: Convection
Tray Dryer Temperature: 40° C.±5° C.
Tray Dryer Relative Humidity (RH): 15% to 30% RH±15%
Drying Time: 24 hr
Bed Depth: ≤2.5 cm FIG. 5 illustrates the residue acetone content as a function of tray-drying time at 40° C./30% RH for 25% Compound A:CAP SDD based on headspace gas chromatography (GC) analysis under conditions having a tray-dryer bed depth of equal to or less than 2.5 cm.

In one example, a spray solution was formed containing 1.25 wt % Compound A, 3.75 wt % CAP, and 95% acetone as follows. Compound A was added to acetone in a stainless-steel solution tank with a top-mounted mixer, and mixed for at least 1 hour. Next, CAP was added directly to this mixture, and the mixture stirred for at least one additional hour. The resulting mixture had a slight haze after the entire amount of polymer had been added. This mixture was then filtered by passing it through a filter with a screen size of 230 μm to remove any large insoluble material from the mixture, thus forming the spray solution.

The spray-dried dispersion was then formed using the following procedure. The spray solution was pumped to a spray drier (Niro type XP Portable Spray-Dryer with a Liquid-Feed Process Vessel [PSD-1]) equipped with a pressure swirl atomizer (Spraying Systems Pressure Nozzle and Body (SK 76-16)). The PSD-1 was equipped with a 9-inch chamber extension to increase the vertical length of the dryer. The spray drier was also equipped with a diffuser plate having a 1% open area to direct the flow of the drying gas and minimize product recirculation within the spray dryer. The nozzle sat flush with the diffuser plate during operation. The spray solution was pumped to the spray drier at about 215 gm/min at a pressure of about 315 psig. Drying gas (e.g., nitrogen) was circulated through the diffuser plate at an inlet temperature of about 125° C. The evaporated solvent and wet drying gas exited the spray drier at a temperature of 45±5° C. The SDD formed by this process was collected in a cyclone.

Solid non-crystalline dispersions of 10 or 25% Compound A with HPMCAS-MG was also prepared.

Long-term storage of the SDD may be at an average of 5° C. (e.g., 2° C. to 8° C.) in double low-density polyethylene (LDPE) bags inside HDPE drums with desiccant between the two bags. The SDD may be stored for short-term, e.g., 1 week, at ambient temperature and humidity (e.g., 25° C./60% RH).

Example 10

In vitro Analysis of Spray-Dried Dispersion Formulation with 25% of Compound A

1. Physical Properties

Table 6 lists the general physical properties of a 25% Compound A:CAP SDD manufactured from an acetone solution.

TABLE 6

Physical Properties of 25% Compound A:CAP SDD

| Parameter | Value |
|---|---|
| Morphology | Smooth collapsed spheres |
| Appearance | White powder |
| Volumetric mean particle diameter D(4,3) (μm) | 25 |
| $DV_{10}$, $DV_{50}$, $DV_{90}$ *(μm) | 8, 22, 48 |
| Span ($DV_{90}$ − $DV_{10}$)/$DV_{50}$ | 1.9 |
| Bulk specific volume (cc/g) | 7.5 |
| Tapped specific volume (cc/g) | 3.7 |
| Glass-transition temperature ($T_g$) (° C.) | 114 |
| Crystallinity | non-crystalline |

*10 vol % of the particles have a diameter that is smaller than $D_{10}$; 50 vol % of the particles have a diameter that is smaller than $D_{50}$, and 90 vol % of the particles have a diameter that is smaller than $D_{90}$.

2. Potency/Purity

The potency and purity of the SDD were assessed by high-performance liquid chromatography (HPLC), which indicated that SDD prepared from an acetone solution did not significantly change the purity of Compound A and the potency was similar to the theoretical potency of the formulation.

3. Dissolution Performance

In vitro performance was evaluated using an in vitro dissolution test performed at a theoretical $C_{max}$ of 200 μg/mL of Compound A in NaTC/POPC in PBS (pH 6.5), wherein $C_{max}$ is maximum observed concentration; NaTC/POPC is 3.7/1 sodium taurocholate/l-palmitoyl-2-oleoyl-sn-glycero-3-phosphocholine and PBS is phosphate buffer solution. Samples were weighed, dissolved in the buffer system, centrifuged, and the supernatant analyzed by HPLC at 10, 20, 40, and 90 minutes.

Figure 6:
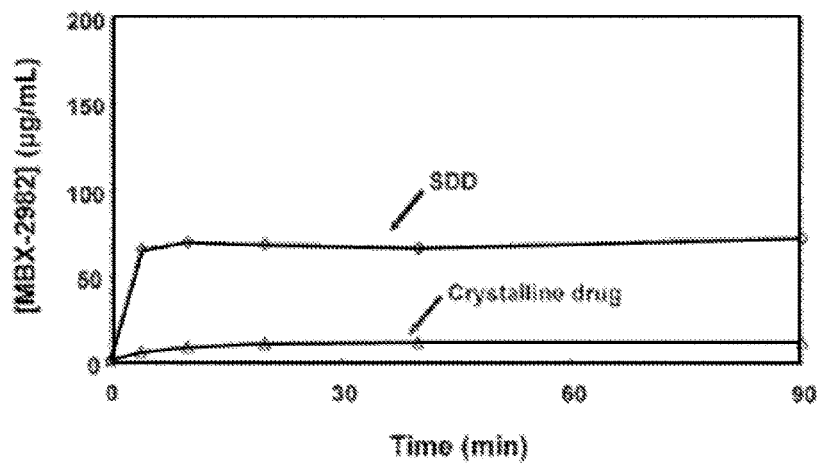
FIG. 6 provides the in vitro dissolution results for the 25% Compound A:CAP SDD and crystalline Compound A.

Tables 7a and 7b and FIG. 6 compares in vitro dissolution performance of Compound A:CAP SDD with that of crystalline of Compound A, HPMCAS-MG, and HPMCAS-HG. As the figure shows, the $C_{max}$ and $AUC_{0-90}$ (area under the curve through 90 minutes) of the SDD were more than 6-fold higher than those of crystalline of Compound A.

TABLE 7a

| Formulation tested | $C_{max}$ (µg/mL Compound A) | $AUC_{0-90}$ (µg * min/mL) |
|---|---|---|
| 25% Compound A:CAP SDD | 73 | 5,850 |
| Crystalline Compound A | 12 | 950 |

TABLE 7b (Simulated gastric fluid)

| Sample | Polymer | Dose (µg/mL) | $C_{max90}$ (µg/mL) | $AUC_{90}$ (min * µg/mL) |
|---|---|---|---|---|
| 25% Dispersion | HPMCAS-MG | 200 | 29 | 3600 |
| 25% Dispersion | HPMCAS-HG | 200 | 25 | 3700 |
| 10% Dispersion | HPMCAS-HG | 200 | 26 | 4700 |
| Crystalline | — | 200 | 8 | 1000 |

The concentrations of Compound A obtained in these samples were used to determine the maximum concentration of Compound A ("$C_{max90}$") and the area under the concentration-versus-time curve ("$AUC_{90}$") during the initial ninety minutes.

Example 11

In Vivo Performance

In vivo testing was performed in male dogs to compare the systemic exposure of the 25% Compound A:CAP SDD (n=2) to that of the crystalline Compound A (n=2). As shown in Table 8, the 25% Compound A:CAP SDD provided a enhanced systemic exposure over bulk crystalline drug in male beagle dogs dosed at 10 mg/kg and 200 mg/kg Compound A orally.

TABLE 8

In Vivo Results for 25% Compound A:CAP SDD and Micrometersized Compound A Crystals

| | Crystalline | | SDD | | Enhancement of SDD/ Crystalline | |
|---|---|---|---|---|---|---|
| Dose | $AUC_{0-24\,hr}$ (µg * h/mL) | $C_{max}$ (µg/mL) | $AUC_{0-24\,hr}$ (µg * h/mL) | $C_{max}$ (µg/mL) | AUC | $C_{max}$ |
| 10 mg/kg | 3.9 | 0.56 | 13.9 | 2.24 | 3.6x | 4.0x |
| 200 mg/kg | 17 | 2 | 216 | 11.8 | 12.7x | 5.9x |

Example 12

Tablets

Figure 7:
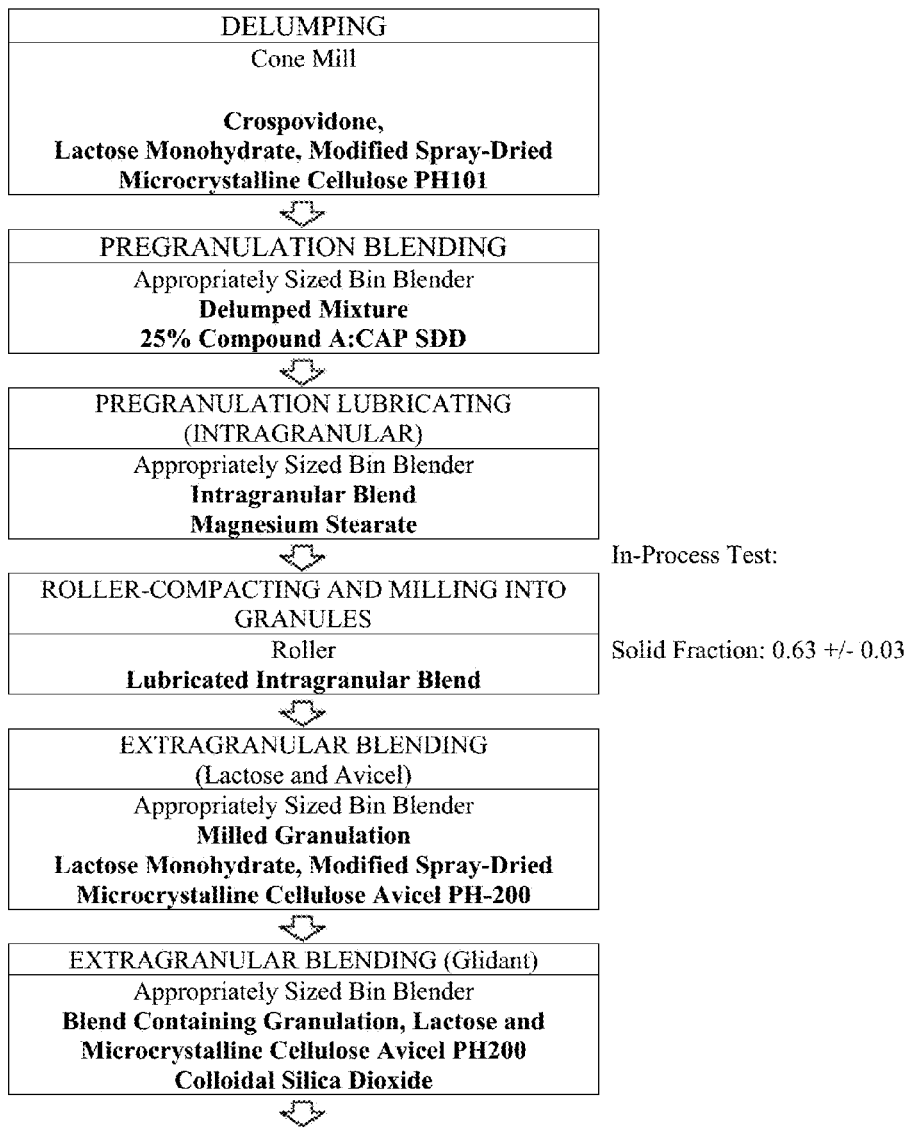
FIG. 7 provides a flow chart for a manufacture process of uncoated Compound A SDD 25 mg tablets.
Figure 7:
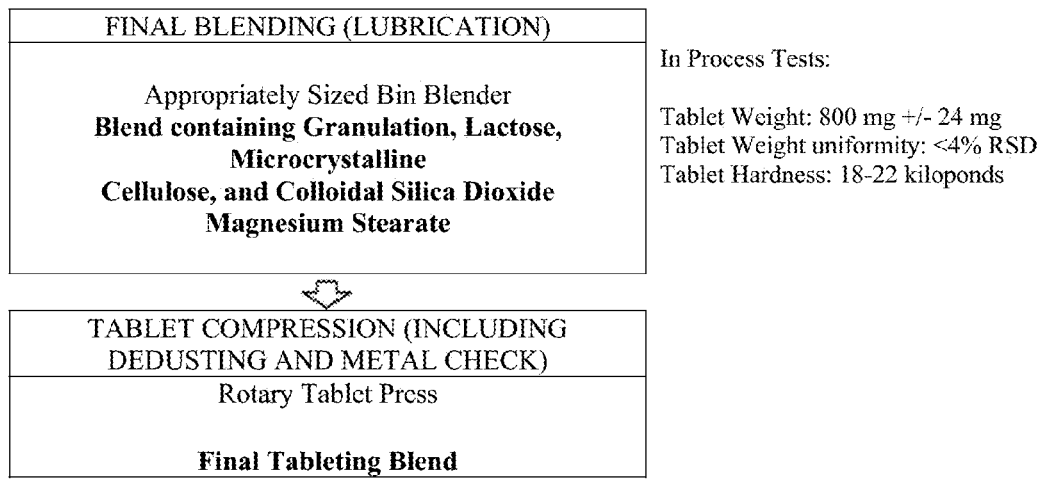
Figure 8:
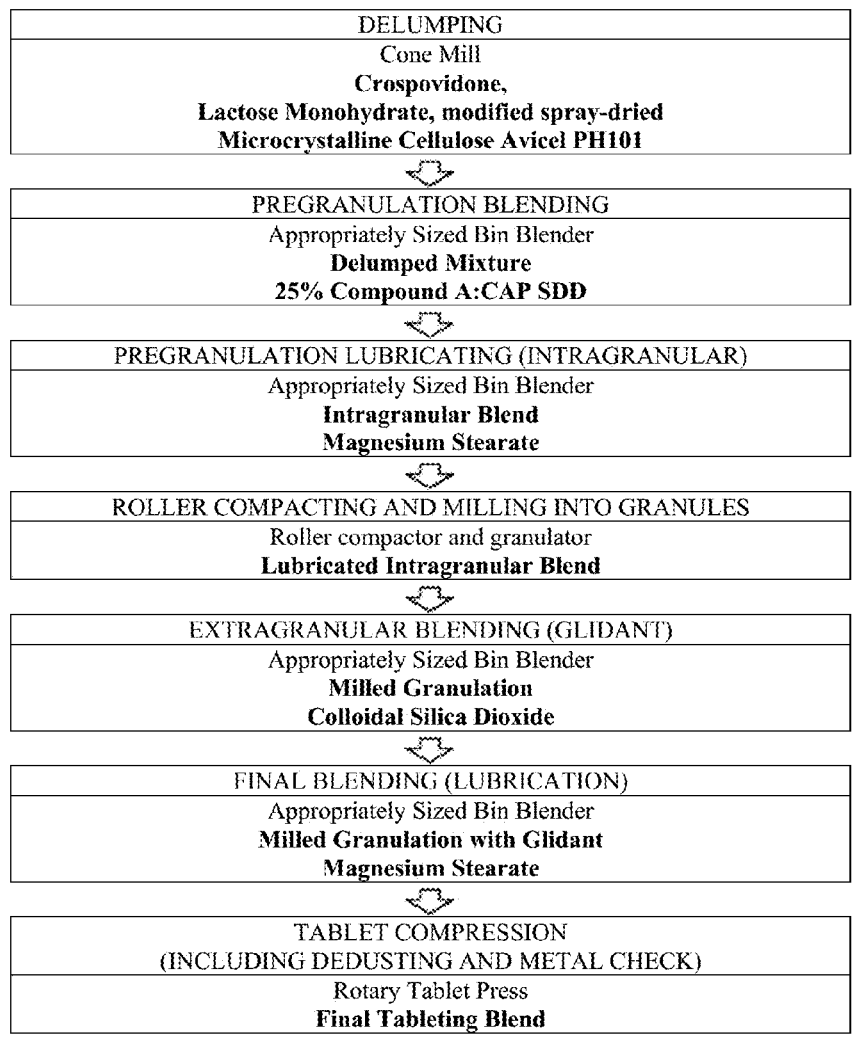
FIG. 8 provides a flow chart for a manufacture process of uncoated Compound A SDD 100 mg tablets.

Tablet manufacture includes blending the SDD and intragranular excipients to form a uniform blend, dry-granulating to form flowable granules, blending extragranular excipients to provide additional tableting functionality, tablet compressing to form unit dosages, and film-coating to provide a white opaque coating. The excipients used in the 25 and 100 mg tablets are shown in Tables 9 and 10, respectively. A sufficient amount of the solid dispersion of compound A was used to provide for 25 mg of the compound in the 25 mg tablet, and a sufficient amount of the solid dispersion of compound A was used to provide for 100 mg of the compound in the 100 mg tablet. FIG. 7 provides an overview of the manufacturing process for the uncoated 25 mg tablets. FIG. 8 provides an overview of the manufacturing process for the uncoated 100 mg tablets.

TABLE 9

Composition of 25 mg Tablet

Compound A
Microcrystalline cellulose (Avicel PH-101, FMC); intragranular
Lactose monohydrate, modified spray-dried (316 FastFlo, Foremost); intragranular
Crospovidone (Polyplasdone XL, ISP); intragranular
Magnesium stearate (vegetable sourced); intragranular
Crospovidone (Polyplasdone XL, ISP); extragranular
Lactose monohydrate, modified spray-dried (316 FastFlo, Foremost); extragranular
Microcrystalline cellulose (Avicel PH-200, FMC); extragranular
Colloidal silica dioxide (Cab-O-Sil M5P, Cabot); extragranular
Magnesium stearate (vegetable sourced); extragranular

TABLE 10

Composition of 100 mg Tablet
Component

Compound A
Microcrystalline cellulose (Avicel PH-101, FMC); intragranular
Lactose monohydrate, modified spray-dried (316 FastFlo, Foremost); intragranular
Crospovidone (Polyplasdone XL, ISP); intragranular
Magnesium stearate (vegetable sourced); intragranular
Colloidal silica dioxide (Cab-O-Sil M5P, Cabot); extragranular
Magnesium stearate (vegetable sourced); extragranular The same blending and dry-granulation process is used for the 25 mg and 100 mg active tablets (i.e., a "common granulation" is used for both tablet strengths). The 25 and 100 mg uncoated tablets may have identical size, shape and weight. Optionally, the 25 mg and 100 mg tablets can be coated using a film coating compositions well known to those of skill in the art, for example, Opadry II (white 85F18378, Colorcon) and purified water.

Dry Granulation

The dry granulation process is carried out as follows:
1. The intragranular excipients are delumped by passing through a low-shear cone mill.
2. The delumped excipients, and the 25% Compound A:CAP SDD are added to the bin blender and blended.
3. The magnesium stearate is hand screened with a portion of the blend from step 2 into the bin blender and blended.
4. The blend is discharged from the blender and roller-compacted. The roller compactor parameters are established to provide roller compacted material with a solid fraction (a unitless relative density parameter) of 0.63. This is assured by in-process measurement.
5. The roller compacted material is granulated by passing through a 0.8 mm oscillating screen mill. The granulation from step 5 is called the "Common Granulation" and is used to manufacture both the 25 and 100 mg active tablets.

The extragranular final blend and tablet compression are carried out as follows:
1. The required amounts of extragranular excipients are calculated.
2. For the 25 mg active tablets only, the granulation, extragranular lactose and extragranular microcrystalline cellulose are added to the bin blender and blended.
3. The colloidal silica dioxide is hand screened with a portion of the blend from step 2 into the bin blender and blended.

4. The magnesium stearate is hand screened with a portion of the blend from step 3 into the bin blender and blended.
5. The powder is discharged from the blender and compressed into 800 mg total weight tablets using a rotary tablet press. The tablet weight, tablet weight distribution and tablet hardness are adjusted during startup and are monitored at timed intervals during compressing to assure product attributes are met.
6. The tablets are de-dusted, passed through a metal detector and stored in double polyethylene bags in drums.

In-process controls of tablet preparation:
Tableting—Dry Granulation: Solid Fraction (Relative Granulation Density): 0.63±0.03 (dimensionless).
Tableting—Compression:
  Appearance: Absence of visual defects
  Mean Tablet Weight: Working Range±3% of Target, Alert Range±6% of Target
  Weight Uniformity: <4% RSD
  Tablet Hardness: Working Range 18-22 kP, Alert Range 16-24 kP.

In one particular example, crospovidone, lactose monohydrate, and microcrystalline cellulose were delumped using a comil 197 equipped with a 0.032-inch (032R) screen and 1601 impellor. The spray-dried dispersion was added to the delumped mixture and blended using a PK twin-shell blender, followed by addition and blending of the magnesium stearate, to form the intragranular blend. Next, the intragranular blend was roller compacted and milled into granules using a Gerteis Mini-Pactor with a Gerteis Star Rotor Mill with a 0.8 mm screen, a compression force between 4 and 7 kN/cm, and a roll speed between 2 and 6 rpm. The milled granulation was blended with colloidal silica dioxide, followed by the addition and blending of the extragranular magnesium stearate. Tablets were compressed using a Kilian T-100 rotary press with 0.3586"×0.7174" modified oval tooling to a hardness of 17-23 kP.

Example 13

Film-Coating of Tablets

Figure 9:
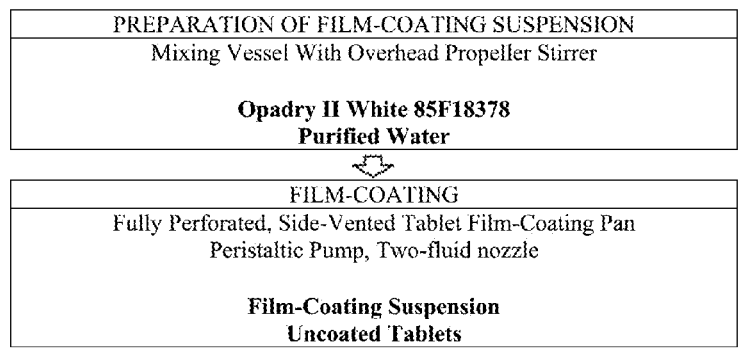
FIG. 9 provides a process flow chart for film coating of uncoated Compound A SDD (spray dried dispersion) 25 and 100 mg tablets.

The aqueous film-coating process is the same for the 25 and 100 mg active tablets, which is described below and illustrated in FIG. 9.
1. The Opadry II powder is added to Purified Water and stirred until no lumps remain.
2. The coating pan is pre-warmed and then the empty pan is spray-coated with a thin layer of Opadry II to eliminate sliding of tablets during film-coating.
3. Tablets are added to the pan and pre-warmed.
4. The tablets are film-coated and the coating suspension is stirred throughout the coating process to prevent settling.
5. When the coating process is complete, the tablets are dried with jog tumbling.
6. Finished, coated tablets are stored in double polyethylene bags in drums.

In one particular example, a coating solution was formed by adding Opadry II to purified water (1:9 wt:wt) in a mixing vessel with overhead propeller stirrer. The coating solution was pumped using a peristaltic pump to a Schlick 970 spray gun with 1.0-mm nozzle and standard air cap, and the tablets were coated in a Vector LDCS pan-coater. The following conditions were used: atomizing air pressure 15 psi, nozzle tip-to-bed distance 2.5", inlet air flow 45 CFM, inlet-air temperature 70 to 75° C., exhaust temperature 46° C., pan run speed 20 rpm, and solution flow rate 9 g/min. Coated tablets had a hardness of 20 kP.

Sink Dissolution Test

A sink dissolution test was performed on 100-mgA Film-Coated SDD tablets. 900 mL dissolution media (0.05 M $NaH_2PO_4$, pH 6.8, containing 1 wt % sodium lauryl sulfate) was added to 1000 mL VanKel dissolution vessels and allowed to warm up for about 30 minutes. Tests were performed at 37° C. Four tablets were dropped into individual vessels containing the dissolution media at time 0. The theoretical maximum concentration of Compound A in the dissolution media was 11 µg/mL. Samples (10 mL) were taken at 5, 15, 30 and 45 minutes using 20 mL syringes with cannulas equipped with 10 µm full flow filters. The samples were filtered through a 0.45 µm nylon syringe filter into an HPLC vial for analysis. The results are shown in Table 11. The 100 mg tablets released 98.3% of theoretical by 45 minutes. Tablets were greater than 80% dissolved within 5 minutes.

TABLE 11

Sink Dissolution of 100-mg Film-Coated SDD Tablets (average of 4 tablets)

| | 100-mg Film-Coated SDD Tablets | | | |
|---|---|---|---|---|
| Time (min) | Average Compound A Released (mg) | Std dev (mg) | Average % released (of theoretical) | Std dev % released |
| 0 | 0.0 | 0.0 | 0.0 | 0.0 |
| 5 | 81.8 | 0.7 | 81.8 | 0.7 |
| 15 | 96.2 | 0.1 | 96.2 | 0.1 |
| 30 | 93.6 | 5.9 | 93.6 | 5.9 |
| 45 | 98.3 | 0.2 | 98.3 | 0.2 |

The tablets can be packed in high-density polyethylene (HDPE) bottles with polypropylene heat-induction seal caps and desiccant. Bottles can be labeled with the lot number, content, storage conditions and other information as required.

Example 14

In Vivo Results

Methodology:
Study Design
This is a single center, phase 1, double-blind, placebo-controlled, multiple ascending dose study of Compound A given orally as a reformulated tablet (spray dried dispersion, or SDD) to otherwise healthy subjects with "pre-diabetes" (impaired fasting glucose, impaired glucose tolerance, or HbA1C≥5.8), or diet-controlled type 2 diabetes mellitus. The study was designed to evaluate the safety, tolerability, pharmacokinetics (PK), and proof-of-concept pharmacodynamics of Compound A. Each dosing cohort consisted of a screening period to assess eligibility, a dosing and observational period, and a follow-up period.

The screening visit was used to assess preliminary eligibility in potential subjects who provided informed consent. Final eligibility for study enrollment was determined after check-in to the clinic on Day −3, before randomization and dosing (on Day 1). Eleven eligible subjects who successfully completed screening were enrolled into the lowest dose cohort that was yet to be filled, and randomly assigned in a double-blind fashion to receive Compound A (n=8) or matched placebo (n=3). Up to 4 additional subjects were admitted to the clinic and available as back-ups in the event that 1 of the original 11 subjects was not dosed for any reason.

Each of these study cohorts was enrolled and completed independently, and in sequential fashion. After completion of the inpatient observational period at Day 8, blinded clinical safety and laboratory parameters (including PK) were assessed in a teleconference between the Principal Investigator, or Sub-Investigator, and the Metabolex Medical Monitor, after which subject dosing assignments could have been unblinded, if necessary, for determination of dose-limiting toxicities (DLTs). If two dose-limiting toxicities (DLTs) occurred within the same treatment cohort in subjects receiving active drug, no further dose escalation would have been allowed, and the maximum tolerated dose (MTD) would have been defined by the dose in the previous cohort. Additionally, dosing may have been halted at the discretion of the sponsor depending on observed Compound A concentrations and PK parameters from the preceding cohort in context of the safety and pharmacodynamic profile of the preceding cohorts.

Study Procedures

Screening Phase (Day −35 to −3)

The initial screening visit occurred between Day −35 and Day −4, before the start of each new dose cohort, to determine subject eligibility. At the initial screening visit, subjects signed an informed consent prior to any study specific assessments or assignment of a screening number. Screening evaluations included collection of demographics and a full medical history with medication review, 12-lead ECG and vital signs (including height and weight), drug and alcohol screen, serum pregnancy test (females only), clinical laboratory evaluation and HbA1c. A minimum of 15 subjects who satisfied initial screening eligibility assessments were invited to complete the Day −3 assessments. Subjects returned to the clinic three days prior to scheduled drug administration (Day −3) for a repeat safety and final eligibility evaluation consisting of vital signs (including weight), ECG, complete physical examination including funduscopic examination, clinical laboratory evaluation, repeat drug and alcohol screen, repeat serum pregnancy test (females only) and review of concomitant medications and interval medical history. Each subject underwent a final eligibility review and up to 15 fully eligible subjects were admitted to the clinic overnight.

Dosing, Observation, and Assessment Period (Day −2 to Day 8)

On Day −2, following a 10 hour overnight fast, up to 15 eligible subjects underwent a baseline MMTT administered between 9:30 and 10:15 am, for the assessment of glucose and insulin response and of total GLP-1 and glucagon. On Day −1, following a 10 hour overnight fast, up to 15 eligible subjects also underwent a baseline OGTT (75 g) administered at the identical time of day as the MMTT, for assessment of the same markers. After the baseline OGTT assessments, 11 subjects were enrolled and randomized into the current dosing cohort. Up to 4 additional subjects remained overnight to be available as back-ups in the event that 1 of the original 11 subjects was, for any reason, not dosed. If more than 11 eligible subjects meet the cohort requirements, the excess subjects may have been included in the next cohort check-in, if within the 35 day screening window and they continued to meet eligibility. On Days 1 through 5, following a 10 hour overnight fast, subjects received daily doses of Compound A or placebo exactly 2 hours earlier than the start of the baseline MMTT, under fasted conditions. The inpatient period in clinic began on Day −2 and concluded on Day 8, following the final inpatient study procedure. The following assessments were made in temporal relationship to the administration of the study drug, administered at Day 1, Time 0, unless otherwise stated:

Pharmacokinetic Blood and Urine Sampling:
Subjects randomized to Compound A or placebo underwent single dose (Day 1) and repeat dose (Day 4) PK. Compound A was measured pre-dose (t −30 and 0 min) on Day 1 and at 20 and 40 minutes, and 1, 2, 3, 4, 6, 8, 12, and 24 hours post-dose. Compound A was measured at identical timepoints associated with the Day 4 dose, but included additional measurements at 48 and 72 hours post-dose (Day 7). Additionally, a 24 hour urine collection was completed on Day 4 for potential measurement of Compound A and its metabolites.

Safety Assessments:
AE's: reviewed and recorded just before study drug administration and twice daily during the inpatient observational period (through Day 8)
Complete physical examination including funduscopic examination: Day 6
Vital signs: Days −2, −1, Days 1 through 5 (immediately pre-dose and at 15, 30, and 60 minutes and 2, 4, and 12 hours post-dose), and Days 6, 7, and 8
ECG: Days 1 through 5 (immediately pre-dose and at 2, 4, and 12 hours post-dose), and Days 6, 7, and 8
Clinical laboratory: on Days 1 (pre-dose), 2, 4, 6, and 8.
Concomitant medication review and recording of all medications used since screening, at every visit beginning at Day −2 and through the observational period.

Pharmacodynamic Blood Sampling:
An MMTT was administered at baseline (Day −2 pre-dose) and at 2 hours after the Day 4 dose, at the identical time on each occasion. Glucose, and insulin were obtained from 7 measurements performed at 30 minutes before the meal, immediately before the meal (0 minutes), and 30, 60, 90, 120, and 240 minutes after starting the meal. Total GLP-1 and glucagon were obtained from 11 measurements performed at 30 minutes before the meal, immediately before the meal (0 minutes), 10, 15, 20, 30, 40, 60, and 90 minutes after starting the meal, and at 2 and 4 hours after starting the meal.
A 75 g OGTT was administered at baseline (Day −1 pre-dose) and at 2 hours after the Day 5 dose, at the identical time on each occasion. Glucose and insulin were obtained from 7 measurements performed at 30 minutes before the glucose ingestion, immediately before the glucose ingestion (0 minutes), and 30, 60, 90, 120, and 240 minutes after the glucose ingestion. Total GLP-1 and glucagon were obtained from 11 measurements performed at 30 minutes before the meal, immediately before the meal (0 minutes), 10, 15, 20, 30, 40, 60, and 90 minutes after starting the meal, and at 2 and 4 hours after starting the meal.
Fasting Glucose: Day 1 pre-dose (2 samples, 5 minutes apart) and Day 5 pre-dose (2 samples, 5 minutes apart)
Remaining sample material was banked for possible, future exploratory analyses related to this compound.

Follow-up Visit (Day 15±1 Days)

This visit included vital signs, full physical examination including funduscopic examination, clinical laboratory evaluation, serum pregnancy test (females only), ECG, concomitant medication review, and review of ongoing AE's. The completion of this visit marked the end of the subject's formal participation in the study.

Number of Patients (Planned):

11 Subjects (8 active, 3 placebo) were to be randomized into the dosing phase of each of the four dosing cohorts of this study, for a total of 44 subjects.

Key Eligibility Criteria
- Healthy, ambulatory, adult male and female volunteers between 18 to 60 years of age with no significant medical history as judged by the Investigator
- History of type 2 diabetes mellitus allowed if diet-controlled and not treated with insulin or oral glucose lowering agents within 3 months of screening
- Fasting glucose≥100 mg/dL and ≤150 mg/dL or 2 hour post OGTT (75 g) glucose>140 mg/dL or HbA1c≥5.8% at screening
- Fasting glucose≤105 mg/dL if HbA1c is <5.8% at screening
- HbA1c between 5.5% and 7.5%
- BMI 25 to 45 kg/m2 (inclusive)
- No prior history of bariatric surgery
- All clinical laboratory test results must have been within normal range or considered not clinically significant
- ECG must have been normal or without clinically relevant pathology as judged by the Investigator; all vital signs including blood pressure must have been within normal limits Investigational Product, Dosage and Mode of Administration:

Compound A (25 mg and 100 mg tablets) or Matched Placebo. Table 12 shows the baseline demographics of the Phase 1c study.

Dose/Route/Regimen:
- Cohort 1: 25 mg (25 mg×1) orally once daily for 5 days
- Cohort 2: 100 mg (100 mg×1) orally once daily for 5 days
- Cohort 3: 300 mg (100 mg×3) orally once daily for 5 days
- Cohort 4: 600 mg (100 mg×6) orally once daily for 5 days Duration of Treatment:
- Screening Period: Up to 33 days (Day −35 to Day −3)
- Dosing and Observational Period: 10 days (Day −2 to Day 8)
- Follow-up Phase: 7 days (Day 9 to Day 15)

TABLE 12

| | Baseline Demographics | | | | |
|---|---|---|---|---|---|
| | Pooled Placebo | Compound A 25 mg | Compound A 100 mg | Compound A 300 mg | Compound A 600 mg |
| N[1] | 11[2] | 8 | 8 | 7[2] | 8 |
| Female (%) | 45% | 38% | 38% | 71% | 38% |
| Age (years) | 44 | 34 | 47 | 42 | 41 |
| Screening FPG (mg/dL) | 95 | 96 | 105 | 110 | 94 |
| Screening 2 h OGTT (mg/dL) | 115 | 136 | 152 | 135 | 120 |
| IFG or IGT[3] N(%) | 4 (36%) | 3 (38%) | 5 (63%) | 3 (43%) | 2 (25%) |
| Screening HbA1C (%) | 6.1 | 6.1 | 6.1 | 6.0 | 6.1 |
| BMI (kg/m2) | 32.2 | 31.3 | 32.2 | 32.9 | 32.5 |

[1]Per Protocol
[2]300 mg Cohort: one active and one placebo subject were excluded due to dosing error
[3]With HbA1c ≥ 6.0%

Pharmacokinetic Results

Figure 10:
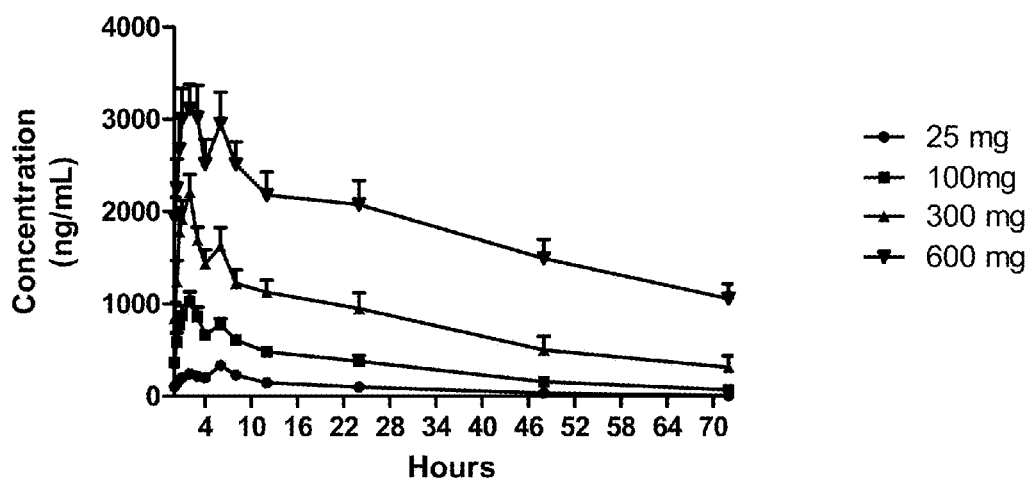
FIG. 10 provides the concentration-time profile after administration of repeat (5) daily doses of compound A to subjects with IFG.
Figure 11:
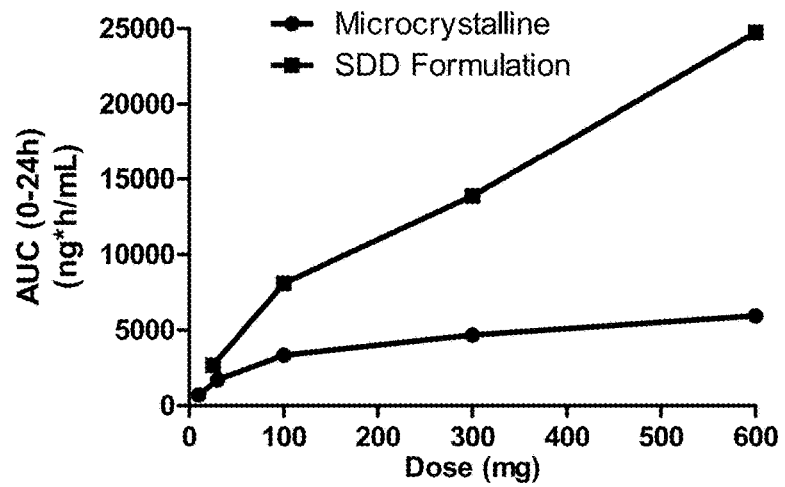
FIG. 11 provides a comparison of the AUC of microcrystalline and SDD (spray dried dispersion) formulation of Compound A as a single dose.
Figure 12:
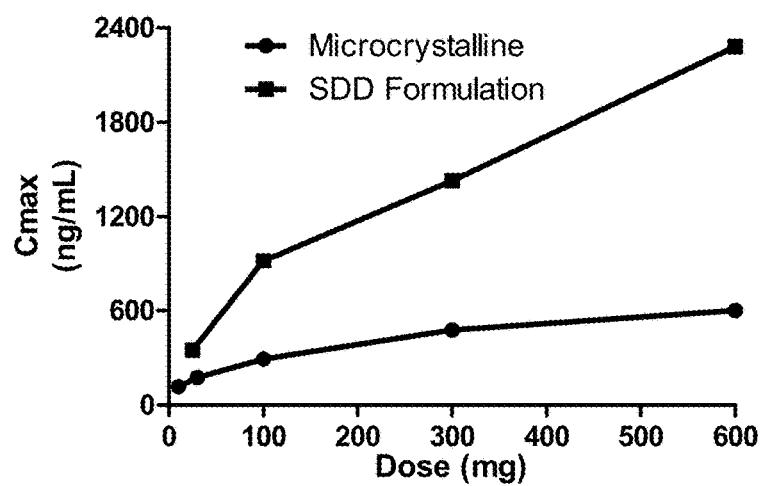
FIG. 12 provides a comparison of Cmax of microcrystalline and SDD (spray dried dispersion) formulation Compound A as a single dose.

In this study, single escalating doses (4 cohorts) of the SDD formulation of Compound A, administered in the fasted state, were well absorbed and led to a relatively linear dose-dependent increase in $C_{max}$ and exposure at all doses administered. Relative to single doses of the microcrystalline formulation, exposure was enhanced by up to 4.2-fold at the top dose (600 mg). Relative to single doses, repeat daily dose PK (Day 5) showed modest accumulation (~2-fold) but by Day 5 steady-state drug levels were nearly achieved. The repeat dose 24 h exposure at the highest dose (600 mg) was ~8-fold higher than the maximum exposure previously achieved with the microcrystalline formulation. The repeat dose half-life was consistent with once daily dosing. A summary of the repeat dose (Day 5) concentration-time profile and PK parameters, by dosing group, is presented in FIG. 10 and Table 13, respectively. A comparison of the AUC and $C_{max}$ for the SDD formulation and the microcrystalline formulation are shown in FIGS. 11 and 12, respectively.

TABLE 13

Mean (±SD) Pharmacokinetic Parameters after Administration of Repeat (5) Daily Doses of Compound A to Healthy Subjects with Pre-Diabetes

| Parameter (Units) | Treatment | | | | Microcrystalline |
|---|---|---|---|---|---|
| | 25 mg | 100 mg | 300 mg | 600 mg | 600 mg |
| $C_{max}$ (ng/mL) | 346 (127) | 1153 (228) | 2330 (558) | 3565 (835) | 437 |
| $T_{max}$ (hr) | 5.4 (1.8) | 2.8 (2.1) | 2.2 (1.8) | 3.3 (1.8) | N/A |
| $T_{1/2}$ (hr) | 14.0 (4.53) | 18.3 (8.92) | 15.3 (3.03) | N/A | N/A |
| $AUC_{0-24\,h}$ (ng * hr/mL) | 4150 (2412) | 13336 (2706) | 30027 (9148) | 57859 (16152) | 7000 |
| $AUC_{0-inf}$ (ng * hr/mL) | 6497 (5026) | 24618 (10835) | 45019 (14068) | N/A | N/A |

Pharmacodynamic Results

In the studies that have been conducted to date, Compound A consistently lowered fasting plasma glucose (FPG) and glucose excursion following a mixed meal tolerance test (MMTT) and oral glucose tolerance test (OGTT). Single doses of the microcrystalline formulation of Compound A (600 mg and 1000 mg) in study A, and repeat daily doses of 100 mg and 300 mg over 4 days in study B reduced the glucose excursion in a dose-dependent fashion during a mixed meal tolerance test compared to placebo and/or baseline by 20-40%. Repeat daily doses of the SDD formulation of Compound A at all doses tested in study C (25, 100, 300, and 600 mg) reduced the glucose excursion during a mixed meal and oral glucose tolerance test compared to baseline and placebo. The magnitude of the glucose reduction observed during the MMTT was more pronounced, and ranged between 34 and 51%, as shown in FIG. 13. With the SDD formulation, the peak glucose effects appeared to be observed at the 100 and 300 mg doses, while dosing of 600 mg (up to exposures of >50,000 ng*h/mL) did not result in additional glucose lowering in this population of early pre-diabetics. At baseline, subjects in the 600 mg group had better glycemic tolerance than the other groups, which likely explains the apparent lower magnitude of effect at this dose.

Reductions in glucose were greatest in the subsets of subjects with the greatest degree of glucose intolerance at baseline (up to 77% reduction, net of placebo). This is exemplified by a pooled subanalysis of subjects receiving any dose of Compound A in Phase 1c (study C), as depicted in FIG. 14.

What is claimed is:

1. A solid dispersion comprising 5-ethyl-2-{4-[4-(4-tetrazol-1-yl-phenoxymethyl)-thiazol-2-yl]-piperidin-1-yl}-pyrimidine and a water soluble, biologically compatible polymer, wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline, and wherein the water soluble, biologically compatible polymer is cellulose acetate phthalate.

2. The solid dispersion of claim 1, wherein from about 50% to about 100%, from about 75% to about 100%, or about 95% by weight of the 5-ethyl-2-{4-[4-(4-tetrazol-1-yl-phenoxymethyl)-thiazol-2-yl]-piperidin-1-yl}-pyrimidine is non-crystalline.

3. The solid dispersion of claim 1, wherein the smallest diameter of the solid dispersion is from about 1 to about 100 micrometers.

4. The solid dispersion of claim 1, comprising from about 5% to about 75%, from about 10% to about 50%, from about 20% to about 30%, or about 25% by weight 5-ethyl-2-{4-[4-(4-tetrazol-1-yl-phenoxymethyl)-thiazol-2-yl]-piperidin-1-yl}-pyrimidine.

5. The solid dispersion of claim 1, which is a spray-dried dispersion or a hot-melt extrudate.

6. A pharmaceutical formulation comprising a pharmaceutically inert carrier and a therapeutically effective amount of 5-ethyl-2-{4-[4-(4-tetrazol-1-yl-phenoxymethyl)-thiazol-2-yl]-piperidin-1-yl}-pyrimidine free base, wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline and wherein said 5-ethyl-2-{4-[4-(4-tetrazol-1-yl-phenoxymethyl)-thiazol-2-yl]-piperidin-1-yl}-pyrimidine is contained within a solid dispersion which further comprises a water soluble, biologically compatible polymer, wherein the water soluble biologically compatible polymer is cellulose acetate phthalate.

7. The pharmaceutical formulation of claim 6, wherein the composition comprises from about 5% to about 75%, from about 10% to about 50%, from about 20% to about 30%, or about 25% by weight 5-ethyl-2-{4-[4-(4-tetrazol-1-yl-phenoxymethyl)-thiazol-2-yl]-piperidin-1-yl}-pyrimidine.

8. A method of treating a disease or condition selected from the group consisting of Type I diabetes, Type II diabetes and metabolic syndrome, said method comprising administering to a mammal in need of such treatment a therapeutically effective amount of a pharmaceutical formulation of claim 6.

9. The method of claim 8, wherein said disease is Type II diabetes.

10. A method of lowering blood glucose in a mammal, said method comprising administering a therapeutically effective amount of a pharmaceutical formulation of claim 6 to a mammal in need of such treatment.

11. The method of claim 10, wherein blood glucose in a mammal is reduced by about 5% or more, about 25% or more, or about 50% or more.

12. The method of claim 8, wherein said mammal is a human.

13. A method of modulating GPR 119 activity in a cell, said method comprising contacting said cell with a therapeutically effective amount of a pharmaceutical formulation of claim 6.

14. A solid dispersion comprising from about 10% to about 50% by weight of 5-ethyl-2-{4-[4-(4-tetrazol-1-yl-phenoxymethyl)-thiazol-2-yl]-piperidin-1-yl}-pyrimidine and a water soluble, biologically compatible polymer, wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline, and wherein the water soluble, biologically compatible polymer is cellulose acetate phthalate.

15. A pharmaceutical formulation comprising a pharmaceutically inert carrier and from about 10% to about 50% by weight of 5-ethyl-2-{4-[4-(4-tetrazol-1-yl-phenoxymethyl)-thiazol-2-yl]-piperidin-1-yl}-pyrimidine free base, wherein from about 25% to about 100% by weight of the 5-ethyl-2-{4-[4-(4-tetrazol-1-yl-phenoxymethyl)-thiazol-2-yl]-piperidin-1-yl}-pyrimidine is non-crystalline and wherein said 5-ethyl-2-{4-[4-(4-tetrazol-1-yl-phenoxymethyl)-thiazol-2-yl]-piperidin-1-yl}-pyrimidine is contained within a solid dispersion which further comprises a water soluble, biologically compatible polymer, wherein the water soluble biologically compatible polymer is cellulose acetate phthalate.

* * * * *